United States Patent
Schlecht et al.

(10) Patent No.: US 10,413,259 B2
(45) Date of Patent: Sep. 17, 2019

(54) GAP RESOLUTION FOR LINEAR DETECTOR ARRAY

(71) Applicant: Illinois Tool Works, Inc., Glenview, IL (US)

(72) Inventors: Joseph Schlecht, Edina, MN (US); Eric Ferley, Rogers, MN (US); Julien Noel, Puteaux (FR); Roland Le Floc'h, Issy-les-Moulineaux (FR)

(73) Assignee: Illinois Tool Works Inc., Glenview, IL (US)

( * ) Notice: Subject to any disclaimer, the term of this patent is extended or adjusted under 35 U.S.C. 154(b) by 237 days.

(21) Appl. No.: 15/541,307

(22) PCT Filed: Jan. 10, 2016

(86) PCT No.: PCT/US2016/012777
§ 371 (c)(1),
(2) Date: Jun. 30, 2017

(87) PCT Pub. No.: WO2016/122857
PCT Pub. Date: Aug. 4, 2016

(65) Prior Publication Data
US 2017/0367665 A1    Dec. 28, 2017

Related U.S. Application Data

(60) Provisional application No. 62/107,692, filed on Jan. 26, 2015.

(51) Int. Cl.
*G01T 1/36*   (2006.01)
*A61B 6/00*   (2006.01)
(Continued)

(52) U.S. Cl.
CPC ............ *A61B 6/4208* (2013.01); *A61B 6/032* (2013.01); *A61B 6/5258* (2013.01); *A61B 6/585* (2013.01);
(Continued)

(58) Field of Classification Search
CPC ........... A61B 6/03; A61B 6/032; A61B 6/035; G01N 23/046; G01N 2223/419;
(Continued)

(56) References Cited

U.S. PATENT DOCUMENTS

| 6,600,568 B1 | 7/2003 | Lu et al. |
| 9,398,890 B2 | 7/2016 | Dong et al. |

(Continued)

FOREIGN PATENT DOCUMENTS

| JP | 2000199702 A | 7/2000 |
| JP | 2008200580 A | 9/2008 |

(Continued)

OTHER PUBLICATIONS

Response to Communication pursuant to Rules 161(1) and 162 EPC dated Sep. 1, 2017, from counterpart European Patent Application No. 16706026.8, filed on Feb. 22, 2018, 22 pp.
(Continued)

*Primary Examiner* — David P Porta
*Assistant Examiner* — Mamadou Faye
(74) *Attorney, Agent, or Firm* — Shumaker & Sieffert, P.A.

(57) ABSTRACT

An imaging system generates a first radiograph based on a first pattern of radiation detected by a Linear Diode Array (LDA) radiation detector positioned to detect a radiation beam emitted by a radiation generator. The LDA radiation detector comprises a plurality of modules. Each respective module of the plurality of modules comprises a respective plurality of photodiodes corresponding to pixels. Further-
(Continued)

more, the imaging system may determine, based on the first radiograph, a size of a gap between two of the modules of the LDA radiation detector. After determining the size of the gap, the imaging system may generate a second radiograph based on a second pattern of radiation detected by the LDA radiation detector. The imaging system may generate a third radiograph by modifying, based on the size of the gap, the second radiograph to compensate for the gap.

27 Claims, 18 Drawing Sheets

(51) Int. Cl.
    *G01N 23/04*      (2018.01)
    *G01T 1/20*      (2006.01)
    *A61B 6/03*      (2006.01)

(52) U.S. Cl.
    CPC ........... *G01N 23/04* (2013.01); *G01T 1/2018* (2013.01); *A61B 6/4233* (2013.01); *A61B 6/4429* (2013.01); *A61B 6/482* (2013.01); *A61B 6/583* (2013.01)

(58) Field of Classification Search
    CPC ..... G01V 5/005; G06T 11/003; G06T 11/005; G06T 11/006; G06T 11/008; G06T 2207/10081
    See application file for complete search history.

(56) References Cited

U.S. PATENT DOCUMENTS

| | | | |
|---|---|---|---|
| 2007/0147585 A1* | 6/2007 | Eilbert | G01N 23/04 378/57 |
| 2008/0292057 A1* | 11/2008 | Finkler | G01T 1/2928 378/98.8 |
| 2012/0093280 A1 | 4/2012 | Konno et al. | |
| 2013/0322605 A1 | 12/2013 | Kosarev | |

FOREIGN PATENT DOCUMENTS

| | | |
|---|---|---|
| JP | 2009118943 A | 6/2009 |
| JP | 2014147757 A | 8/2014 |

OTHER PUBLICATIONS

International Search Report and Written Opinion from International Application No. PCT/US2016/012777, dated May 4, 2016, 12 pp.

\* cited by examiner

GAP RESOLUTION FOR LINEAR DETECTOR ARRAY

This application claims the benefit of U.S. Provisional Patent Application No. 62/107,692, filed Jan. 26, 2015, the entire content of which is incorporated herein by reference.

TECHNICAL FIELD

This disclosure relates to x-ray digital radiography and computed tomography.

BACKGROUND

X-ray digital radiography (DR) is a commonly used non-invasive and non-destructive imaging technique using digital x-ray detectors, such as flat-panel detectors, charge-coupled device (CCD) cameras, or complementary metal-oxide-semiconductor (CMOS) cameras, or linear diode arrays (LDAs). X-ray computed tomography (CT) is a procedure that uses computer-processed x-rays radiographs acquired at different view angles to produce 3-dimensional (3D) images of an object. A tomographic image of an object is an image of a conceptually two-dimensional "slice" of the object. A computing device may use the tomographic images of the object to generate a 3-dimensional image of the object. X-ray CT may be used for industrial purposes to conduct non-destructive evaluation of objects.

SUMMARY

In one example, this disclosure describes a method for generating radiographs. The method comprises generating, by an imaging system, a first radiograph based on a first pattern of radiation detected by a Linear Diode Array (LDA) radiation detector positioned to detect a radiation beam emitted by a radiation generator. The LDA radiation detector comprises a plurality of modules. Each respective module of the plurality of modules comprises a respective plurality of photodiodes corresponding to pixels. The method further comprises determining, by the imaging system, based on the first radiograph, a size of a gap between two of the modules of the LDA radiation detector. The method also comprises after determining the size of the gap. Additionally, the method comprises generating, by the imaging system, a second radiograph based on a second pattern of radiation detected by the LDA radiation detector. The method also comprises generating, by the imaging system, a third radiograph by modifying, based on the size of the gap, the second radiograph to compensate for the gap.

In another example, this disclosure describes an imaging system comprising: a radiation generator. The imaging system also comprises a LDA radiation detector positioned to detect a radiation beam emitted by the radiation generator. In this example, the LDA radiation detector comprises a plurality of modules. Each of the modules comprises a respective plurality of photodiodes corresponding to pixels. The imaging system also comprises one or more processors operatively coupled to the LDA radiation detector. In this example, the one or more processors are configured to generate a first radiograph based on a first pattern of radiation detected by the LDA radiation detector. Furthermore, in this example, the one or more processors are configured to determine, based on the first radiograph, a size of a gap between two of the modules of the LDA radiation detector. In this example, the one or more processors are also configured such that, after determining the size of the gap, the one or more processors generate a second radiograph based on a second pattern of radiation detected by the LDA radiation detector. Furthermore, in this example, the one or more processors generate a third radiograph by modifying, based on the size of the gap, the second radiograph to compensate for the gap.

In another example, this disclosure describes a non-transitory computer-readable data storage medium having instructions stored thereon that, when executed, cause an imaging system to generate a first radiograph based on a first pattern of radiation detected by a LDA radiation detector positioned to detect a radiation beam emitted by a radiation generator. In this example, the LDA radiation detector comprises a plurality of modules. Each respective module of the plurality of modules comprises a respective plurality of photodiodes corresponding to pixels. In this example, the instructions further cause the imaging system to determine, based on the first radiograph, a size of a gap between two of the modules of the LDA radiation detector. Furthermore, in this example, after determining the size of the gap, the instructions cause the imaging system to generate, based on a second pattern of radiation detected by the LDA radiation detector, a second radiograph. Additionally, in this example, the instructions cause the imaging system to generate a third radiograph by modifying, based on the size of the gap, the second radiograph to compensate for the gap.

In another example, this disclosure describes a method for generating radiographs. The method comprises generating, by an imaging system, a first radiograph based on a first pattern of radiation detected by a 2-dimensional radiation detector positioned to detect a radiation beam emitted by a radiation generator. The 2-dimensional radiation detector comprises a plurality of modules. Each respective module of the plurality of modules comprises a respective plurality of photodiodes corresponding to pixels. The method further comprises determining, by the imaging system, based on the first radiograph, a size of a gap between two of the modules of the 2-dimensional radiation detector. The method also comprises after determining the size of the gap. Additionally, the method comprises generating, by the imaging system, a second radiograph based on a second pattern of radiation detected by the 2-dimensional radiation detector. The method also comprises generating, by the imaging system, a third radiograph by modifying, based on the size of the gap, the second radiograph to compensate for the gap.

In another example, this disclosure describes an imaging system comprising: a radiation generator. The imaging system also comprises a 2-dimensional radiation detector positioned to detect a radiation beam emitted by the radiation generator. In this example, the 2-dimensional radiation detector comprises a plurality of modules. Each of the modules comprises a respective plurality of photodiodes corresponding to pixels. The imaging system also comprises one or more processors operatively coupled to the 2-dimensional radiation detector. In this example, the one or more processors are configured to generate a first radiograph based on a first pattern of radiation detected by the 2-dimensional radiation detector. Furthermore, in this example, the one or more processors are configured to determine, based on the first radiograph, a size of a gap between two of the modules of the 2-dimensional radiation detector. In this example, the one or more processors are also configured such that, after determining the size of the gap, the one or more processors generate a second radiograph based on a second pattern of radiation detected by the 2-dimensional radiation detector. Furthermore, in this example, the one or more processors generate a third radiograph by modifying, based on the size of the gap, the second radiograph to compensate for the gap.

In another example, this disclosure describes a non-transitory computer-readable data storage medium having instructions stored thereon that, when executed, cause an imaging system to generate a first radiograph based on a first pattern of radiation detected by a 2-dimensional radiation detector positioned to detect a radiation beam emitted by a radiation generator. In this example, the 2-dimensional radiation detector comprises a plurality of modules. Each respective module of the plurality of modules comprises a respective plurality of photodiodes corresponding to pixels. In this example, the instructions further cause the imaging system to determine, based on the first radiograph, a size of a gap between two of the modules of the 2-dimensional radiation detector. Furthermore, in this example, after determining the size of the gap, the instructions cause the imaging system to generate, based on a second pattern of radiation detected by the 2-dimensional radiation detector, a second radiograph. Additionally, in this example, the instructions cause the imaging system to generate a third radiograph by modifying, based on the size of the gap, the second radiograph to compensate for the gap.

The details of one or more examples are set forth in the accompanying drawings and the description below. Other features, objects, and advantages will be apparent from the description, drawings, and claims.

DETAILED DESCRIPTION

Figure 1:
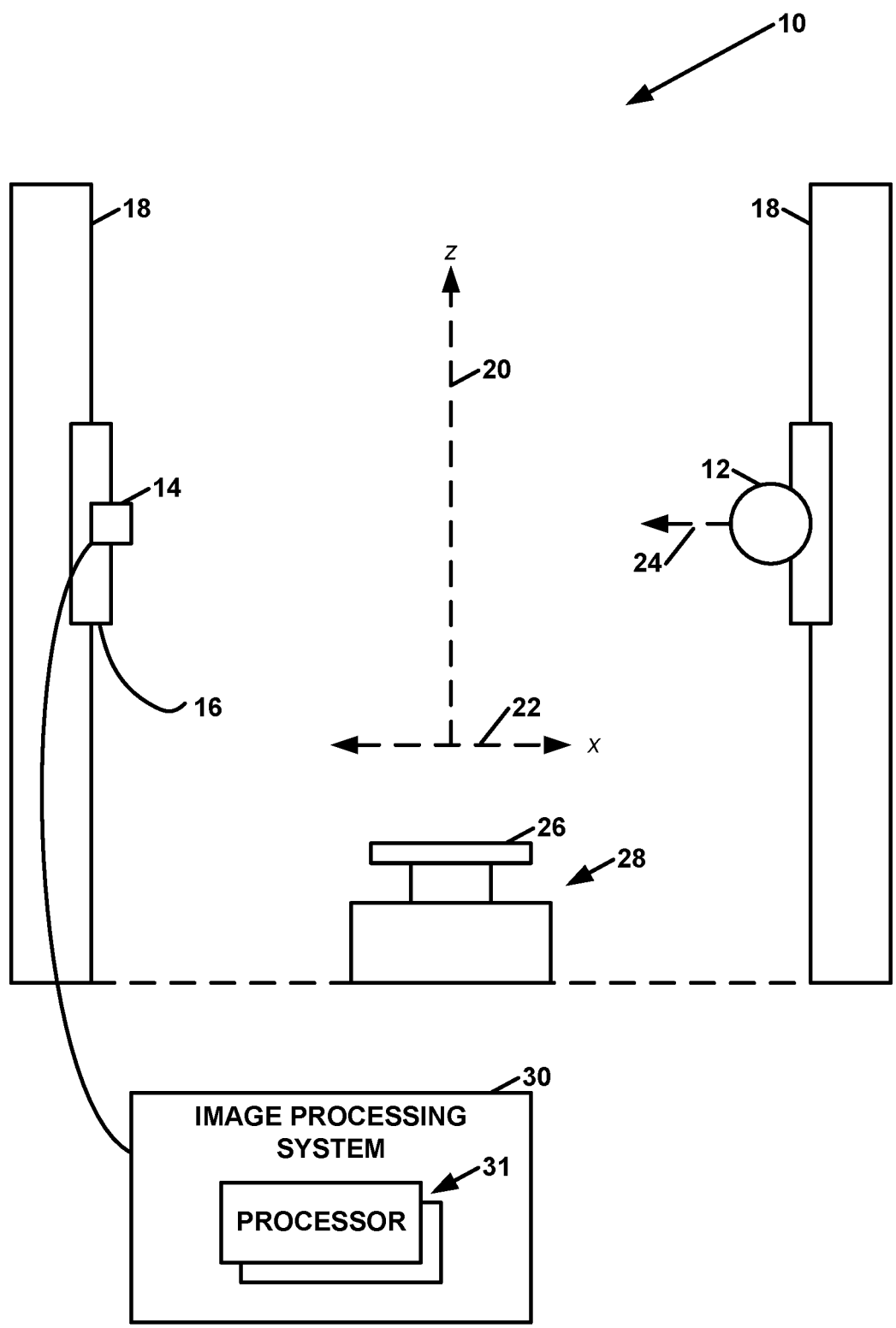
FIG. 1 is a schematic drawing of an example x-ray imaging system, in accordance with one or more techniques of this disclosure.

In general, this disclosure relates to calibration of an x-ray imaging system to compensate for gaps between modules of a linear diode array (LDA) x-ray detector. The LDA x-ray detector detects x-rays generated by an x-ray source of the x-ray imaging system and outputs electrical signals corresponding to a pattern of detected x-rays. An image processing system of the x-ray imaging system generates a radiograph based on the electrical signals output by the LDA x-ray detector. Furthermore, the image processing system may generate a computed tomography (CT) image based on radiographs. In this way, the x-ray imaging system can be used for x-ray radiography and CT. X-ray radiography and CT are methods of non-invasively or non-destructively obtaining three-dimensional structures in medical imaging and industrial non-destructive evaluation (NDE).

As indicated above, the x-ray imaging system may comprise an LDA x-ray detector. The LDA x-ray detector includes a 1-dimensional array of photodiodes. Each of the photodiodes corresponds to a different pixel. For instance, there may be a 1-to-1 relationship between photodiodes and pixels. The 1-dimensional array of photodiodes may be divided into a plurality of modules. In this case, each of the modules comprises a different subset of the photodiodes. Due to manufacturing limitations, there may be gaps in the LDA x-ray detector between modules. Such gaps may be wider than gaps between photodiodes within a module. When the x-ray imaging system is used to generate a radiograph, the gaps between modules of the LDA x-ray detector may result in visible artifacts (i.e., inaccuracies). Furthermore, when radiographs generated by the x-ray imaging system are used to generate a computed tomography (CT) image, the artifacts may cause the CT image to be blurry.

One or more techniques of this disclosure calibrate the x-ray imaging system such that the x-ray imaging system is able to compensate for the gaps between modules of the LDA x-ray detector. As a result, radiographs generated by the x-ray imaging system may contain fewer defects and CT images generated from such radiographs may be sharper.

In accordance with one or more examples of this disclosure, the x-ray imaging system may generate a first radiograph based on a first pattern of x-rays detected by the LDA x-ray detector positioned to detect an x-ray beam emitted by an x-ray generator. The generated pattern of x-rays may comprise an array of pixels. In some examples, lighter pixels in the array of pixels correspond to locations where x-rays were blocked by an object and darker pixels in the array of pixels correspond to locations where x-rays were not blocked. Furthermore, the imaging system may determine, based on the first radiograph, a size of a gap between two of the modules of the LDA x-ray detector. After determining the size of the gap, the imaging system may generate a second radiograph based on a second pattern of x-rays detected by the LDA radiation detector. The imaging system may generate a third radiograph by modifying, based on the size of the gap, the second radiograph to compensate for the gap.

For instance, the x-ray imaging system may move a target object through an x-ray beam emitted by an x-ray generator. The target object moves along a path at a consistent speed in a first dimension without moving in a second dimension and a third dimension. The first, second, and third dimensions are mutually orthogonal. The first dimension is parallel to an orientation of an LDA x-ray detector positioned to detect the x-ray beam. The third dimension is parallel to an axis between the x-ray generator and the LDA x-ray detector. The LDA x-ray detector comprises a plurality of modules. Each respective module of the plurality of modules comprises a respective plurality of photodiodes corresponding to pixels. Furthermore, the x-ray imaging system may generate, based on a first pattern of x-rays detected by the LDA x-ray detector, a first radiograph comprising a line corresponding to the target object as the target object moves along the path. The x-ray imaging system may determine, based on sizes and positions of discontinuities in a slope of the line, sizes and positions of gaps between the modules of the LDA x-ray detector. After determining the sizes and positions of the gaps, the x-ray imaging system may generate, based on a second pattern of x-rays detected by the LDA x-ray detector, a second radiograph. The x-ray imaging system may modify the second radiograph to compensate for the sizes and positions of the gaps between the modules of the LDA x-ray detector.

FIG. 1 is a schematic drawing of an example x-ray imaging system 10, in accordance with one or more techniques of this disclosure. As shown in the example of FIG. 1, x-ray imaging system 10 may include an x-ray generator 12 and a linear diode array (LDA) x-ray detector 14. X-ray generator 12 may emit an x-ray beam. Hence, in some instances, this disclosure may refer to x-ray generator 12 or similar devices as "x-ray sources." In some examples, the x-ray beam is cone-shaped. In other examples, the x-ray beam is fan-shaped. In some examples, x-ray generator 12 generates x-rays with an energy range of 20 keV to 600 keV. In other examples, x-ray generator 12 generates x-rays in other energy ranges.

In the example of FIG. 1, LDA x-ray detector 14 is mounted to a detector carriage 16. Detector carriage 16 is mounted to a frame 18. Detector carriage 16 may move in a z-dimension 20 relative to frame 18. Thus, in the example of FIG. 1, detector carriage 16 may move LDA x-ray detector 14 in a vertical direction. LDA x-ray detector 14 may be aligned in z-dimension 20 with x-ray generator 12 when LDA x-ray detector 14 is in use. In the example of FIG. 1, an x-dimension 22 is parallel to an axis 24 (i.e., an x-ray beam axis) between x-ray generator 12 and LDA x-ray detector 14 when LDA x-ray detector 14 is in position to detect an x-ray beam generated by x-ray generator 12. Furthermore, although the example of FIG. 1 shows x-ray generator 12 and LDA x-ray detector 14 mounted to the same frame, x-ray generator 12 and LDA x-ray detector 14 may, in other examples, be mounted to separate frames. Thus, x-ray generator 12 and LDA x-ray detector 14 may be mounted to one or more frames. In some examples, x-ray generator 12 and LDA x-ray detector 14 may generate and detect other forms of radiation, and hence may be referred to as a radiation generator and a radiation detector, respectively. Hence, it will be understood that discussion of x-rays in this disclosure may be applicable to other forms of radiation, such as visible light.

Furthermore, in the example of FIG. 1, LDA x-ray detector 14 comprises a 1-dimensional array of photodiodes. In other words, LDA x-ray detector 14 comprises a single row of photodiodes. This disclosure may refer to the spatial orientation of the row of photodiodes of LDA x-ray detector 14 as the orientation of LDA x-ray detector 14. Each of the photodiodes corresponds to a different pixel. Thus, the energy of an x-ray photon hitting a photodiode may correspond to the brightness of a pixel corresponding to the photodiode. The 1-dimensional array of photodiodes is divided into a plurality of modules. Thus, each of the modules comprises a different subset of the photodiodes. For example, LDA x-ray detector 14 may comprise 2,000 photodiodes arranged in a straight line. In this example, LDA x-ray detector 14 may comprise 10 modules, each having 200 photodiodes.

Each respective module of LDA x-ray detector 14 may include a layer of scintillation material, such as Cesium Iodide fabricated on amorphous silicon on a glass detector array. The scintillator layer of a module absorbs x-rays and emits visible light photons that are, in turn, detected by a photodiodes of the module. While the photodiodes may actually detect visible light generated by x-ray photons absorbed by the scintillator layer, this disclosure may, for ease of explanation, refer to the photodiodes detecting x-rays or x-ray photons hitting photodiodes. The detector pixel size may range from tens to hundreds of micrometers. In some examples, the pixel size of LDA x-ray detector 14 may be in the range of 25 micrometers to 250 micrometers. In other words, although each pixel may be represented as a single point, each pixel may actually correspond to an area specified by the pixel size of the pixel (e.g., 25 micrometers to 250 micrometers).

Due to manufacturing limitations, there may be gaps in LDA x-ray detector 14 between modules. For instance, LDA x-ray detector 14 may be manufactured by assembling multiple pre-assembled modules. Because each respective module is initially a separate component, each respective module may comprise extra material at either end of the respective module in order to prevent damage to the photodiodes at either end of the respective module during manufacturing and assembly. For each respective gap, the width of the respective gap (i.e., the size of the respective gap) may be greater than a width between two adjacent photodiodes within a module.

In the example of FIG. 1, x-ray imaging system 10 comprises an image processing system 30. Image processing system 30 may comprise a computing system. Example types of computing systems may include personal computers, server computers, mainframe computers, laptop computers, special-purpose computers, and so on. As shown in the example of FIG. 1, image processing system 30 may include one or more processors 31. Each of processors 31 may comprise one or more digital signal processors (DSPs), general purpose microprocessors, application specific integrated circuits (ASICs), field programmable logic arrays (FPGAs), or other equivalent integrated or discrete logic circuitry. For ease of explanation, this disclosure may describe actions performed by one or more of processors 31 as being performed by image processing system 30. Image processing system 30, and hence processors 31, are operatively coupled to various components of x-ray imaging system 10 such that processors 31 are able to output electrical signals to such components and receive electrical signals from such components. Such electrical signals may represent commands, image data, status data, and so on. Although this disclosure discusses electrical signals and the example of FIG. 1 shows a cable connecting image processing system 30 to a component in x-ray imaging system 10, such signals may be optical signals and/or wirelessly transmitted signals.

When LDA x-ray detector 14 detects a pattern of x-rays emitted by x-ray generator 12, LDA x-ray detector 14 may output electrical signals corresponding to the pattern of x-rays. Image processing system 30 may interpret the electrical signals to generate one or more radiographs.

X-ray imaging system 10 may comprise one or more manipulator mechanisms configured to a move an object relative to x-ray generator 12 and LDA x-ray detector 14. In some examples, one or more processors 31 of image processing system 30 output signals to move the object relative to x-ray generator 12 and LDA x-ray detector 14. For instance, in the example of FIG. 1, an object may be mounted (or otherwise positioned) on a stage 26 disposed between x-ray generator 12 and LDA x-ray detector 14. In the example of FIG. 1, stage 26 is mounted to a stage manipulation mechanism 28. Stage manipulation mechanism 28 may move stage 26 (and thus an object mounted on stage 26) parallel to z-dimension 20. Additionally, in some examples, stage manipulation mechanism 28 may move stage 26 (and thus an object mounted on stage 26) parallel to a y-dimension that is mutually orthogonal to x-dimension 22 and z-dimension 20. Thus, in the example of FIG. 1, they-dimension is oriented directly into and out of the page. In some examples, stage manipulation mechanism 28 may concurrently move stage 26 (and thus an object mounted on stage 26) in z-dimension 20 and the y-dimension.

Furthermore, in some examples, stage manipulation mechanism 28 rotates stage 26 with an axis of rotation parallel to z-dimension 20 (i.e., perpendicular to x-ray beam axis 24). Thus, stage 26 may be configured to carry and rotate an object. Consequently, x-ray imaging system 10 may acquire radiographs at different projection angles as the object is rotated in an x-ray beam generated by x-ray generator 12. In some examples, x-ray imaging system 10 acquires radiographs at different rotation angles and processes the radiographs to assemble the radiographs into a 3-dimensional radiograph of the object. Furthermore, in some examples, stage manipulation mechanism 28 rotates stage 26 while concurrently moving stage 26 linearly in z-dimension 20.

As indicated briefly above, LDA x-ray detector 14 comprises a plurality of modules. Each of the modules comprises a 1-dimensional array of photodiodes. Gaps may exist between the modules of LDA x-ray detector 14. These gaps can cause errors in radiographs generated by x-ray imaging system 10 if not corrected. These errors are compounded when generating a CT image from the radiographs, resulting in blurriness. The gaps between modules of different LDA x-ray detectors of different x-ray imaging systems may differ in size and position. Thus, one cannot assume that the sizes and positions of gaps between modules of LDA x-ray detectors are the same in all x-ray imaging systems.

Techniques of this disclosure may enable x-ray imaging system 10 to compensate for the gaps between modules of LDA x-ray detector 14. In accordance with one example technique of this disclosure, a user mounts a target object on stage 26. The target object may be various types of objects. For example, the target object may be a pin, rod, sphere, cone, or other type of object.

Furthermore, in this example, x-ray imaging system 10 may move, relative to x-ray generator 12 and LDA x-ray detector 14, the target object along a path at a consistent speed in the y-dimension without moving the target object in z-dimension 20 and without moving the target object in x-dimension 22. For instance, the target object may move, relative to x-ray generator 12 and LDA x-ray detector 14, at a consistent speed, along a path in a plane parallel to an orientation of LDA x-ray detector 14. As the target object moves along the path, the target object moves through an x-ray beam emitted by x-ray generator 12. In some examples, the plane is orthogonal to an axis between x-ray generator 12 and LDA x-ray detector 14.

The movement of the target object relative to x-ray generator 12 and LDA x-ray detector 14 may be achieved in several different ways. For example, stage manipulation mechanism 28 may move stage 26 (and thus the target object mounted to stage 26) in the y-dimension, relative to frame 18, without moving x-ray generator 12 and LDA x-ray generator 14 relate to frame 18. In this example, processors 31 may be configured to activate one or more manipulator mechanisms, such as stage manipulation mechanism 28, to move the target object relative to the one or more frames without moving the radiation generator and the LDA radiation detector relative to the one or more frames. In another example, x-ray generator 12 and LDA x-ray detector 14 synchronously move in the y-dimension, relative to frame 18. Thus, moving the target object relative to x-ray generator 12 and LDA x-ray detector 14 may comprise moving both x-ray generator 12 and LDA x-ray detector 14 relative to frame 18 without moving the target object relative to frame 18. In this example, processors 31 may be configured to activate the one or more manipulator mechanisms to move both the radiation generator and the LDA radiation detector relative to the one or more frames without moving the target object relative to the one or more frames. In another example, another mechanism, such as a carriage or robotic arm, may move the target object relative to x-ray generator 12 and LDA x-ray detector 14. This mechanism may be specifically designed for the calibration process of this disclosure. In some instances, the mechanism may be removed from x-ray imaging system 10 after calibration.

Figure 6:
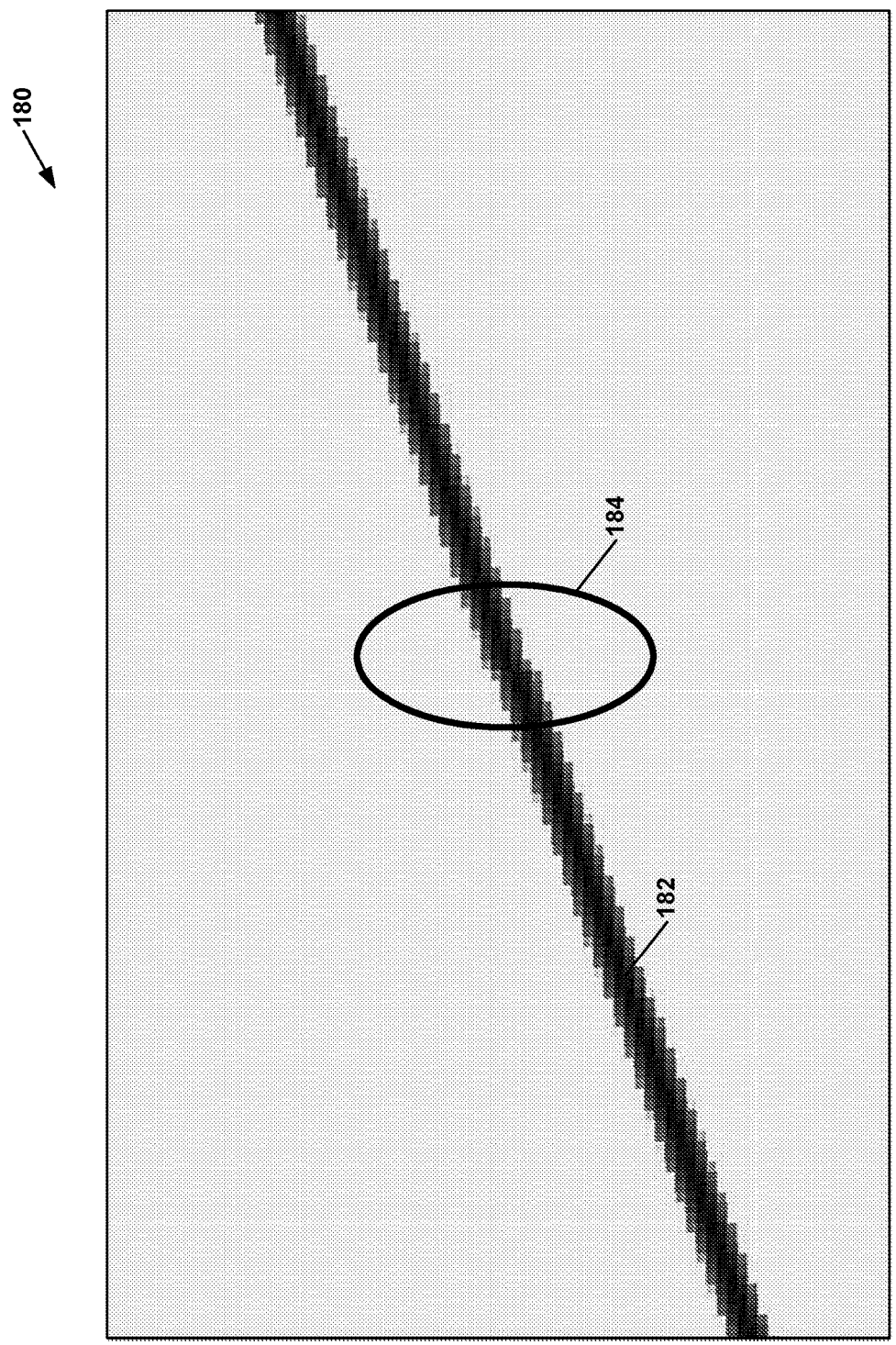
FIG. 6 is an example radiograph showing an artifact caused by a gap between modules of a LDA x-ray detector.

Additionally, image processing system 30 may generate (e.g., acquire), based on a first pattern of x-rays detected by LDA x-ray detector 14, a first radiograph comprising a line corresponding to the target object as the target object moves along the path. The first radiograph may be a time-lapse image of the target object moving along the path. Thus, although the target object may only block x-rays at a few points along the path at any given time, the cumulative effect of moving the target object along the path is a line in the resulting time-lapse radiograph. FIG. 6, described elsewhere in this disclosure, illustrates an example of such a line. Because each respective row of pixels may correspond to a different respective time and the target object moves relative to LDA x-ray detector 14 in a path aligned with an orientation of LDA x-ray detector 14, the line is diagonal in the resulting time-lapse radiograph. The pattern of x-rays detected by LDA x-ray detector 14 may refer to the energy levels of x-rays, if any, detected by photodiodes of LDA x-ray detector 14.

Furthermore, image processing system 30 may determine, based on sizes and positions of discontinuities in a slope of the line, sizes and positions of gaps between the modules of LDA x-ray detector 14. For example, the positions of the discontinuities in the slope of the line correspond to positions of the gaps between modules of LDA x-ray detector 14. Furthermore, the size of a discontinuity in the slope of the line corresponds to the size of a corresponding gap between modules of the LDA x-ray detector 14. For instance, the larger the size of the discontinuity, the larger the gap size.

After determining the sizes and positions of the gaps, x-ray imaging system 10 may be ready for use. Thus, users may mount various objects on stage 26 for inspection. When a user uses x-ray imaging system 10 to inspect an object, image processing system 30 may generate (e.g., acquire) a second radiograph based on a second pattern of x-rays detected by LDA x-ray detector 14. Because image processing system 30 has determined the sizes and positions of the gaps between modules of LDA x-ray detector 14, image processing system 30 is able to modify the second radiograph to compensate for the sizes and positions of the gaps between the modules of LDA x-ray detector 14.

In some examples, when image processing system 30 modifies a radiograph to compensate for the gaps between the modules of LDA x-ray detector 14, image processing system 30 processes each respective pixel of the radiograph. When x-ray imaging system 10 processes a current pixel, image processing system 30 may determine a total gap size (i.e., gap width) for the current pixel. The total gap size for the current pixel is equal to a sum of the sizes of gaps occurring prior to the pixel in a row of pixels containing the current pixel. In this context, a pixel may be "prior to" the current pixel if the pixel occurs before the current pixel in a scanning order, such as a raster scan order. After determining the total gap size for the current pixel, image processing system 30 estimates a value of the current pixel if the current pixel were shifted by the total gap size for the current pixel. Image processing system 30 may then assign the estimated value to the current pixel. For example, if the value of the current pixel is 20 and the estimated value of the current pixel is 15, image processing system 30 may assign the value 15 to the current pixel is:

In some examples, image processing system 30 may use interpolation to estimate the value of the current pixel. For instance, if the value of a pixel immediately preceding the current pixel is 0 and the value of the current pixel is 1 and the total gap size for the current pixel is 0.5 pixel widths, the estimated value of the current pixel is 0.5. In this example, if the total gap size for the current pixel is 0.75 pixel widths, the estimated value for the current pixel is 0.25. A general formula for determining the estimated value for the current pixel is:

$$y(x') = y_{k-1} + \frac{x' - x_{k-1}}{(x_k + G) - x_{k-1}}(y_k - y_{k-1})$$

In the formula above, $y(x')$ is the estimated value, $y_{k-1}$ is the value of the previous pixel, $x'$ is the position of the estimated value (e.g., defined to be $x_{k-1}+1$), $x_{k-1}$ is the position of the previous pixel, $x_k$ is the position of the current pixel, $G$ is the total gap size for the current pixel, and $y_k$ is the value of the current pixel.

Although the examples above only use the values of the current pixel and the previous pixel, other techniques for determining an estimated value of the current pixel may involve the values and positions of one or more additional pixels. For instance, image processing system 30 may perform a regression using a series of pixels prior to and/or following the current pixel.

In some examples, x-ray imaging system 10 comprises a conveyor system (e.g., a conveyor belt system). After image processing system 30 determines the sizes and positions of the gaps between modules of LDA x-ray detector 14, users may place objects on the conveyor system. The conveyor system moves the objects between x-ray generator 12 and LDA x-ray detector 14. In this way, image processing system 30 may generate radiographs of objects placed on the conveyor system. Image processing system 30 may modify the radiographs to compensate for the gaps between the modules of LDA x-ray detector 14. In some examples, the conveyor system may move the objects in z-dimension 20. In such examples, x-ray imaging system 10 is installed such that z-dimension 20 and the y-dimension are horizontal directions and x-dimension 22 is the vertical direction. Thus, in such examples, x-ray imaging system 10 may have a configuration similar to the x-ray imaging systems found at airports and other secure facilities for security screening of containers or baggage.

Figure 2:
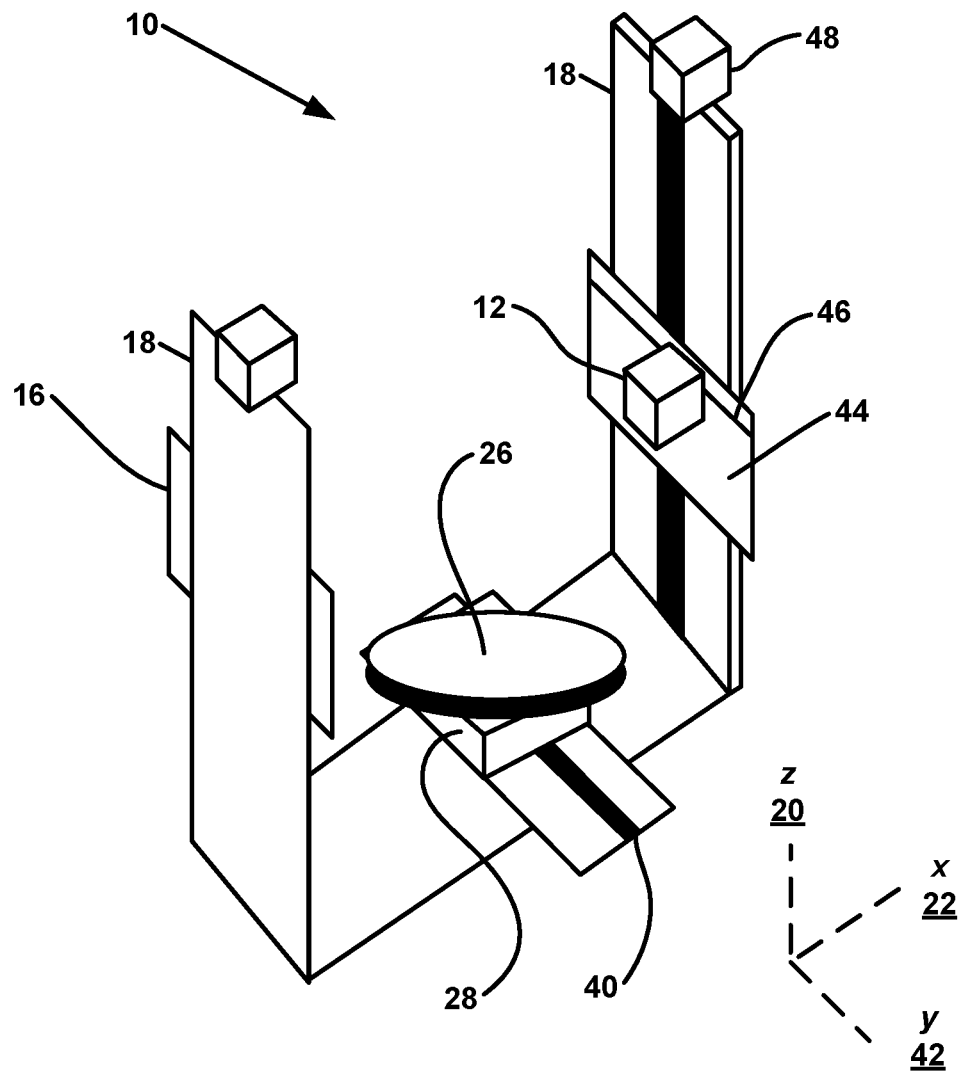
FIG. 2 is an oblique view of the example x-ray imaging system of FIG. 1.

FIG. 2 is an oblique view of x-ray imaging system 10. The example of FIG. 2 illustrates that stage manipulation mechanism 28 comprises a track 40 that enables stage manipulation mechanism 28 to move stage 26 in y-dimension 42. Thus, an object mounted to stage 26 may move linearly in y-dimension 42 relative to x-ray generator 12 and x-ray detector 14. Furthermore, x-ray generator 12 is mounted to a generator carriage 44. A track 46 enables generator carriage 44 (and thus x-ray generator 12) to move linearly in y-dimension 42. Furthermore, a generator manipulation mechanism 48 is configured to move generator carriage 44 (and thus x-ray generator 12) linearly in z-dimension 20.

Figure 3A:
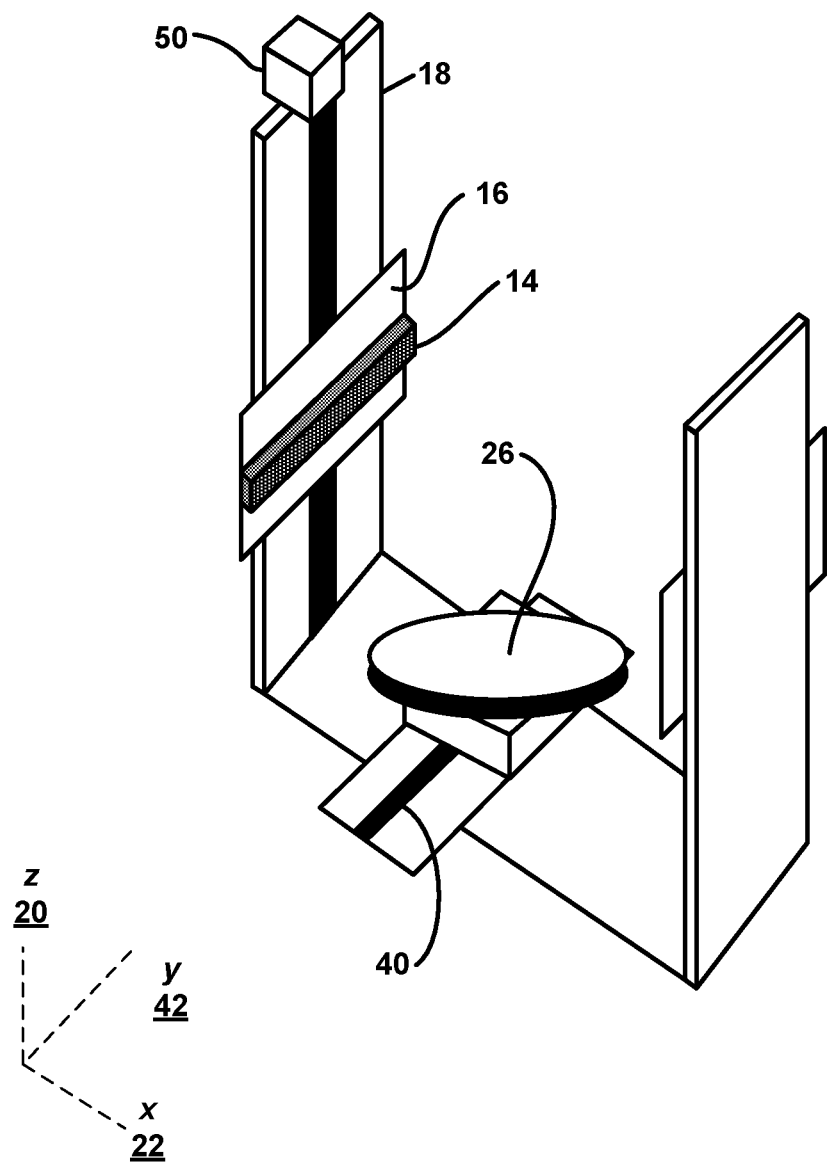
FIG. 3A is a reverse oblique view of the example x-ray imaging system of FIG. 1, having a Linear Diode Array (LDA) x-ray detector.

FIG. 3A is a reverse oblique view of x-ray imaging system 10 having LDA x-ray detector 14. As shown in the example of FIG. 3A, a detector manipulation mechanism 50 is configured to move detector carriage 16 linearly in z-dimension 20. X-ray imaging system 10 may cause generator manipulation mechanism 48 and detector manipulation mechanism 50 to move x-ray generator 12 and LDA x-ray detector 14 synchronously in z-dimension 20. Thus, when x-ray generator 12 and LDA x-ray detector 14 move synchronously in z-dimension 20, an object mounted to stage 26 moves in z-dimension 20 relative to x-ray generator 12 and LDA x-ray detector 14.

Figure 3B:
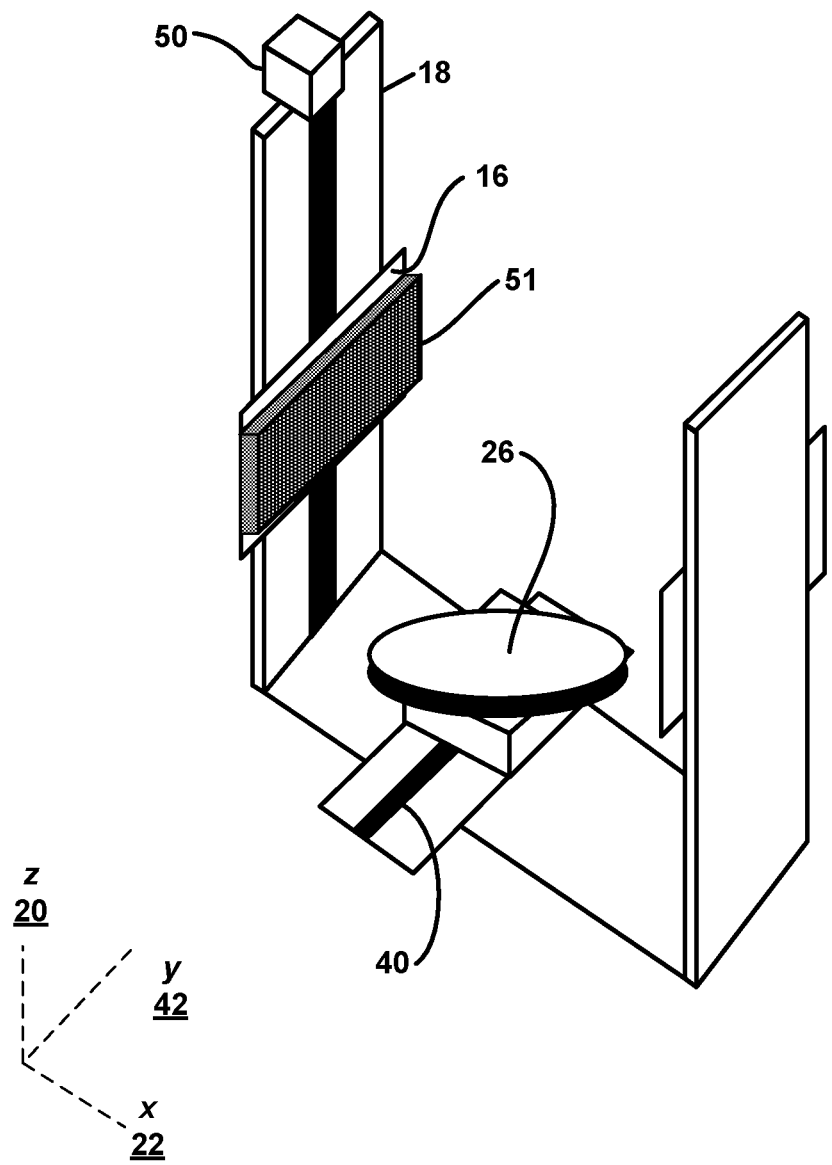
FIG. 3B is a reverse oblique view of the example x-ray imaging system of FIG. 1, having a 2-dimensional x-ray detector.

FIG. 3B is a reverse oblique view of x-ray imaging system 10 having a 2-dimensional (2D) x-ray detector 51. In some examples, 2-dimensional x-ray detector 51 comprises a flat panel detector (FPD). In other examples, x-ray imaging system 10 may comprise a lens-coupled scintillation detector, or another type of x-ray detector, in place of or in addition to the FPD. The FPD may include a layer of scintillation material, such as Cesium Iodide fabricated on amorphous silicon on a glass detector array. In some examples, the pixel size of FPD may be in the range of approximately 25 micrometers to approximately 250 micrometers. Although shown in the example of FIG. 3B as being rectangular, 2D x-ray detector 51 may be square in shape.

High-resolution applications may require lens-coupled detectors that use an optical lens to relay emitted visible light to a detector, such as a charge-coupled device (CCD) or a complementary metal-oxide-semiconductor (CMOS) detector. In some examples, the lens may provide magnification in the range of 1× to 100×, thus making the effective pixel size between 0.1 to 20 micrometers. In some examples where x-ray imaging system 10 comprises a lens-coupled detector, the pixel size of LDA x-ray detector 14 is in a range of 0.1 micrometers to 10 micrometers. Furthermore, in some examples where x-ray imaging system 10 comprises a lens-coupled detector, the field of view may range from 0.2 mm to 25 mm.

Techniques similar to those described elsewhere in this disclosure with regard to an LDA x-ray generator may be applied with regard to 2D x-ray detector 51. In such examples, 2D x-ray detector 51 may be assembled from a plurality of 2D modules. Each of the 2D modules comprises a 2D array of photodiodes. Because the 2D modules may be slightly skewed relative to one another, the gap sizes and positions between the 2D modules may vary from row-to-row and/or column-to-column of a radiograph generated using such a 2D radiation detector. As example of this is shown in FIG. 5B. Hence, compensation of the radiograph to correct for the gaps may involve repeating the techniques described elsewhere in this disclosure for each column and each row of pixels.

In some examples, image processing system 30 may be configured with approximate knowledge of module locations (e.g., a priori knowledge or knowledge acquired through analysis). Furthermore, in this example, x-ray imaging system 10 has the capability to do horizontal and vertical motion over the face of 2D x-ray detector 51. In this example, x-ray imaging system 10 may move a target object that is several pixel sizes wide/high across a vertical or horizontal series of modules and acquire a sequence of radiographs. Because the object is "thick" by several pixels, image processing system 30 may extract a row/column of pixels from the radiographs of the target object, which should be unaffected by any shifting to produce a "sinogram" image (e.g., a concatenation of the extracted rows/columns over time). Image processing system 30 may then use this image to extract gap information (e.g., sizes and positions of gaps) from a linear track of the object, just like the LDA case. This would be done over each set of modules aligned horizontally and vertically in 2D x-ray detector 51. For example, if the modules are arranged in a 4×4 grid (16 modules), x-ray imaging system 10 may repeat the process 8 times. This example assumes edges of the modules are parallel to one another and that the gap information between two adjacent modules is constant.

Figure 4:
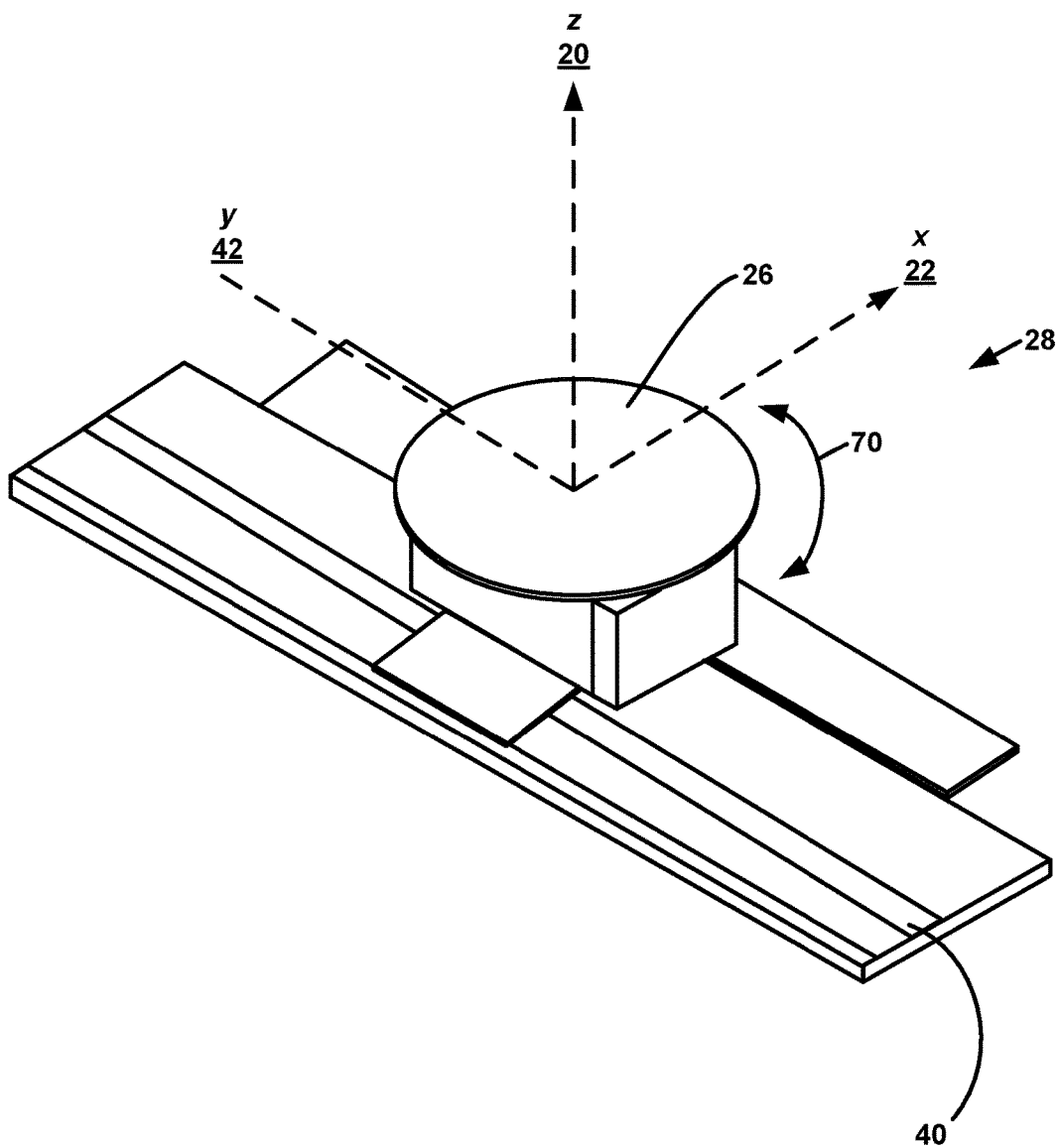
FIG. 4 is an oblique view of a stage manipulation mechanism, in accordance with one or more techniques of this disclosure.

FIG. 4 is an oblique view of stage manipulation mechanism 28, in accordance with one or more techniques of this disclosure. As shown in the example of FIG. 4, stage manipulation mechanism 28 may move stage 26 (and thus an object mounted on stage 26) linearly along track 40 in y-dimension 42. Furthermore, stage manipulation mechanism 28 may rotate stage 26 with an axis of rotation parallel to z-dimension 20, as shown by arrow 70. In other examples, stage manipulation mechanism 28 does not rotate stage 26. Rather, x-ray imaging system 10 may generate 3-dimensional radiographs by rotating x-ray generator 12 and LDA x-ray detector 14 around an object mounted on stage 26. Furthermore, in some examples, stage manipulation mechanism 28 may move stage 26 linearly in z-dimension 20.

Figure 5A:
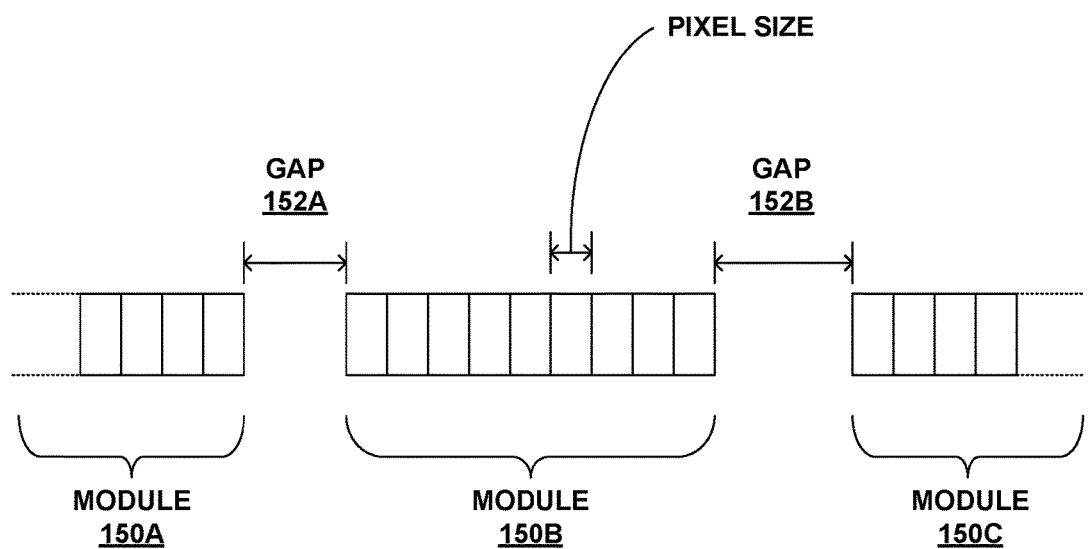
FIG. 5A is a conceptual diagram illustrating example gaps between modules of a Linear Diode Array (LDA) x-ray detector.
Figure 5B:
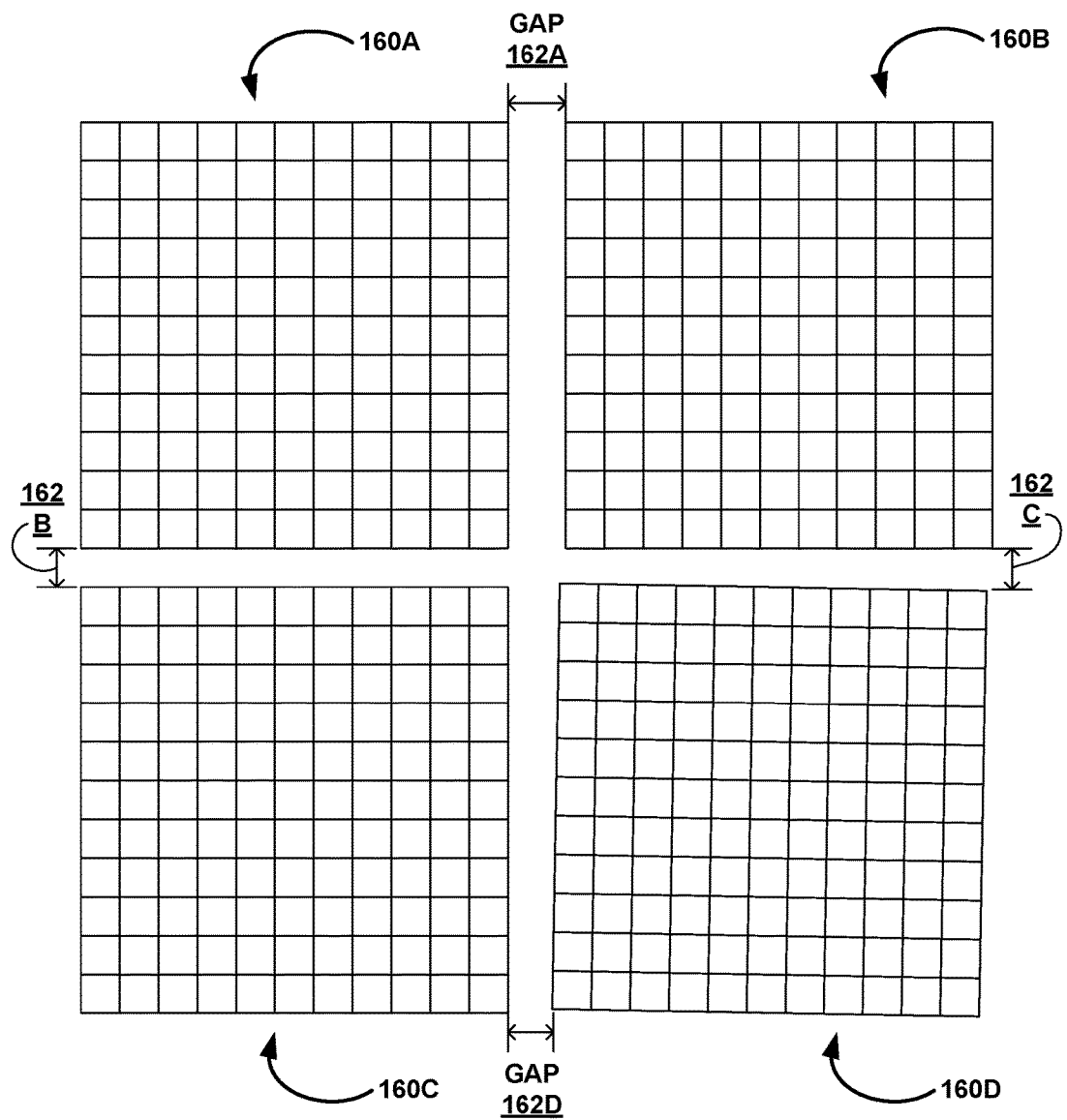
FIG. 5B is a conceptual diagram illustrating example gaps between modules of a 2-dimensional x-ray detector.

FIG. 5A is a conceptual diagram illustrating example gaps between modules of LDA x-ray detector 14. In the example of FIG. 5A, LDA x-ray detector 14 comprises modules 150A, 150B, and 150C (collectively, "modules 150"). Each of modules 150 comprises a linear array of photodiodes. FIG. 5A represents each of the photodiodes as a rectangle. Each of modules 150 may include many more photodiodes than is shown in FIG. 5A. As shown in FIG. 5A, a gap 152A exists between modules 150A and 150B. A gap 152B exists between modules 150B and 150C. Gaps 152A and 152B may cause unwanted artifacts to occur in radiographs generated based on electrical signals generated by LDA x-ray detector 14.

FIG. 5B is a conceptual diagram illustrating example gaps between modules of 2D x-ray detector 51. In the example of FIG. 5B, 2D x-ray detector 51 comprises modules 160A, 160B, 160C, and 160D (collectively, "modules 160"). Each of modules 160 comprises a 2-dimensional array of photodiodes. FIG. 5A represents each of the photodiodes as a small square. Each of modules 160 may include many more photodiodes than is shown in FIG. 5B. As shown in FIG. 5B, a gap 162A exists between modules 160A and 160B, a gap 162B exists between modules 160A and 160C, a gap 162C exists between modules 160B and 160D, and a gap 162D exists between modules 160C and 160D. Gaps 162A, 162B, 162C, and 162D (collectively, "gaps 162") may cause unwanted artifacts to occur in radiographs generated based on electrical signals generated by 2D x-ray detector 51. As shown in the example of FIG. 5B, gaps 162 are necessarily the same size. Moreover, as shown in the example of FIG. 5B, one or more of modules 160 (e.g., module 162D) may be rotated slightly relative to other ones of module 160 such that the sizes of particular gaps may vary. For instance, the sizes of gaps 162C and 162D change from left to right and top to bottom, respectively.

FIG. 6 is a radiograph 180 showing an artifact caused by a gap between modules of LDA x-ray detector 14. Radiograph 180 includes a line 182. Line 182 corresponds to the movement of a target object along a path. When the target object moves along the path, the target object may move at a first consistent speed in a first dimension without moving in a second dimension and without moving in a third dimension. The first, second, and third dimensions are mutually orthogonal. Thus, the first, second, and third dimensions form right angles to one another. The first dimension is parallel to an orientation of LDA x-ray detector 14. The third dimension is parallel to an axis between x-ray generator 12 and LDA x-ray detector 14. In the examples of FIG. 1 through FIG. 4, the second dimension is vertical.

When the target object moves in front of a gap between modules of LDA x-ray detector 14, a discontinuity in the slope of line 182 occurs. For instance, in the example of FIG. 6, line 182 jumps some distance in a vertical direction. Such a discontinuity is shown within oval 184 of FIG. 6. Note that in the example of FIG. 6, the darkest pixels move upward one pixel for every three pixels moved rightward. However, at the discontinuity, the darkest pixels move upward by two pixels.

Figure 7:
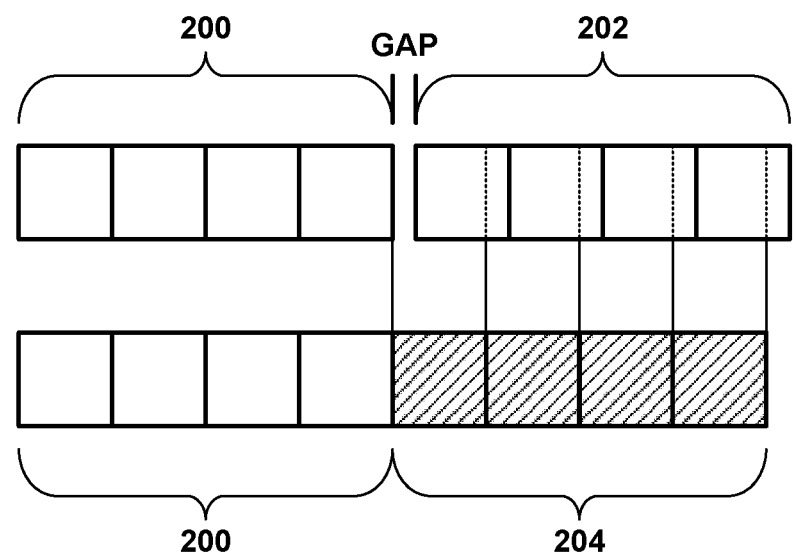
FIG. 7 is a conceptual diagram illustrating an example technique for modifying pixels, in accordance with one or more techniques of this disclosure.

FIG. 7 is a conceptual diagram illustrating an example technique for modifying pixels, in accordance with one or more techniques of this disclosure. In the example of FIG. 7, pixels 200 occur prior to a gap and pixels 202 occur after a gap. After modifying a radiograph containing pixels 200 and 202 to compensator for the gap, pixels 200 may retain their values. However, because pixels 202 are not adjacent to pixels 200, x-ray imaging system 10 may estimate, based on the values of one or more of pixels 200, pixels 202 and the size of the gap, the values of pixels 204 that would be adjacent to pixels 200. X-ray imaging system 10 may use interpolation to estimate the values of pixels 204.

Figure 8A:
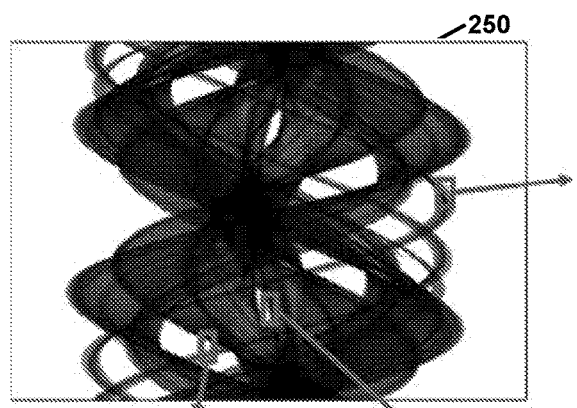
FIG. 8A is an example radiograph containing artifacts caused by one or more gaps between modules of an LDA x-ray detector.
Figure 8B:
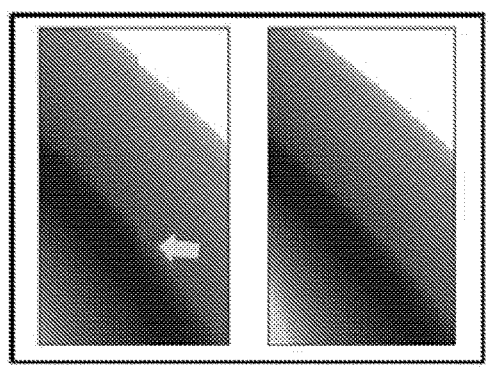
FIG. 8B is an enlarged portion of the example radiograph of FIG. 8A showing an artifact caused by one or more gaps between modules of an LDA x-ray detector and a detailed view of a corrected version of the enlarged portion of the example radiograph, in accordance with one or more techniques of this disclosure.
Figure 8C:
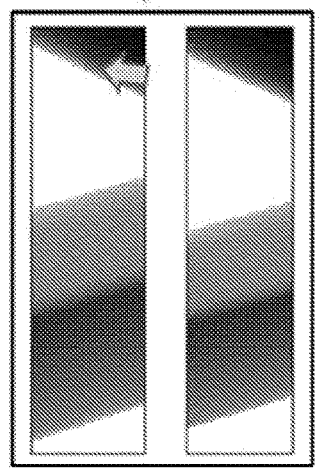
FIG. 8C is an enlarged portion of the example radiograph of FIG. 8A showing an artifact caused by one or more gaps between modules of an LDA x-ray detector and a detailed view of a corrected version of the enlarged portion of the example radiograph, in accordance with one or more techniques of this disclosure.
Figure 8D:
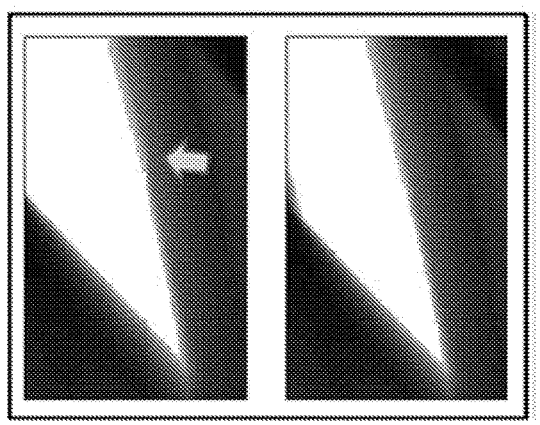
FIG. 8D is an enlarged portion of the example radiograph of FIG. 8A showing an artifact caused by one or more gaps between modules of an LDA x-ray detector and a detailed view of a corrected version of the enlarged portion of the example radiograph, in accordance with one or more techniques of this disclosure.

FIG. 8A is an example radiograph 250 containing artifacts caused by one or more gaps between modules of LDA x-ray detector 14. X-ray imaging system 10 may generate radiograph 250 by rotating an object while moving the object in z-dimension 20. FIG. 8B is an enlarged portion of radiograph 250 showing an artifact caused by one or more gaps between modules of LDA x-ray detector 14 and a detailed view of a corrected version of the enlarged portion of radiograph 250, in accordance with one or more techniques of this disclosure. FIG. 8C is an enlarged portion of radiograph 250 showing an artifact caused by one or more gaps between modules of LDA x-ray detector 14 and a detailed view of a corrected version of the enlarged portion of radiograph 250, in accordance with one or more techniques of this disclosure. FIG. 8D is an enlarged portion of radiograph 250 showing an artifact caused by one or more gaps between modules of LDA x-ray detector 14 and a detailed view of a corrected version of the enlarged portion of radiograph 250, in accordance with one or more techniques of this disclosure.

Figure 9A:
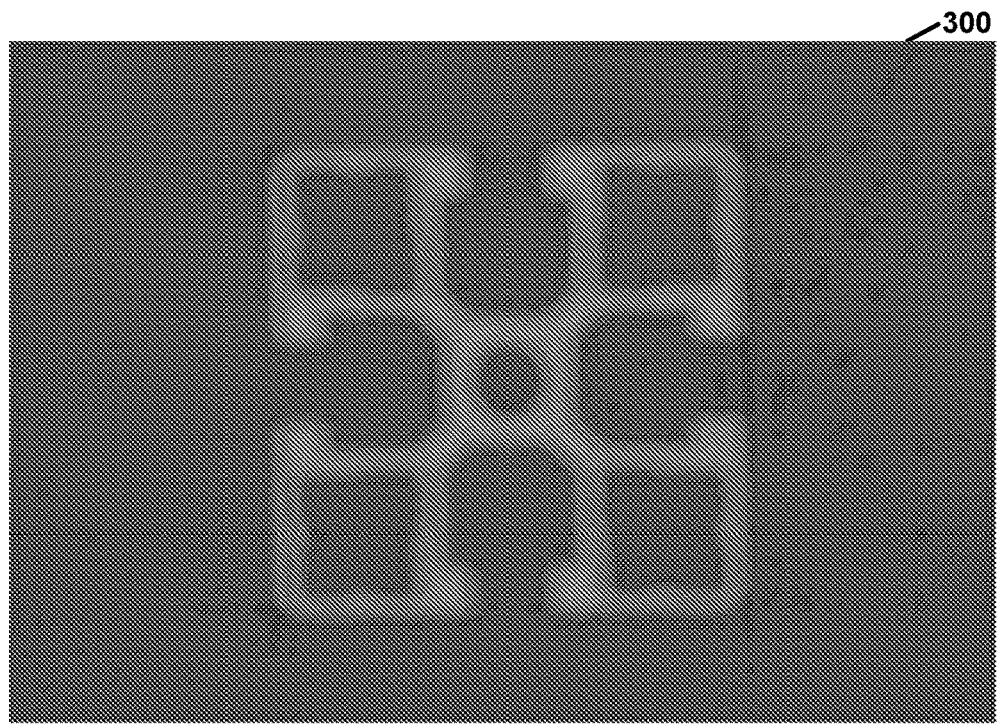
FIG. 9A is an example computed tomography image based on radiographs that are not corrected for artifacts caused by one or more gaps between modules of an LDA x-ray detector.
Figure 9B:
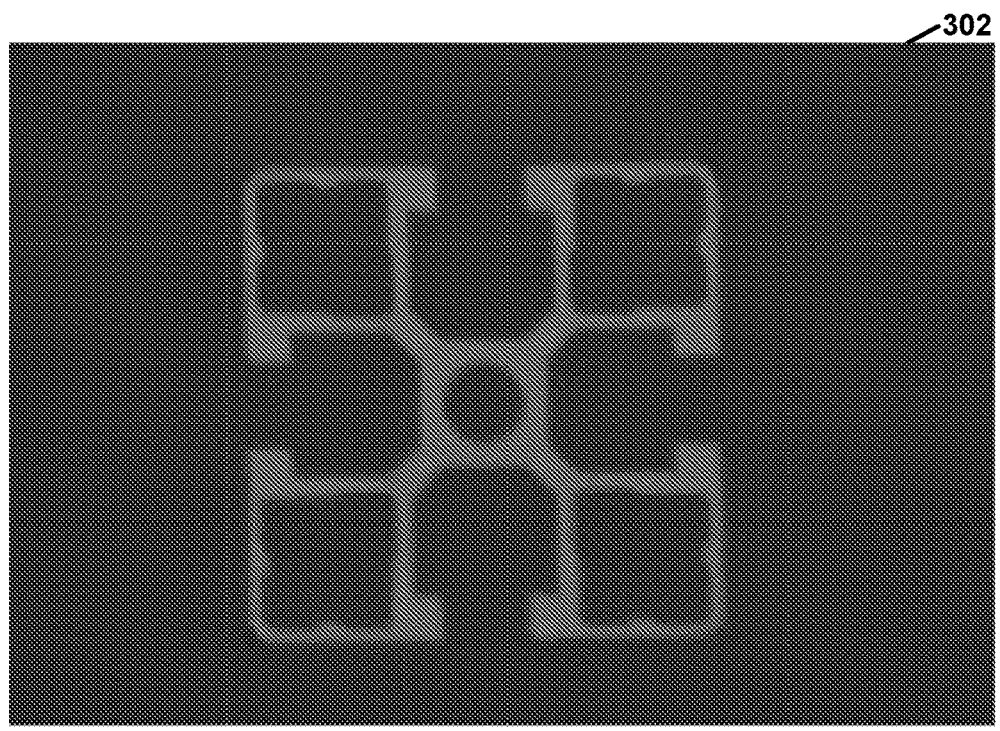
FIG. 9B is an example computed tomography image based on radiographs that are corrected for artifacts caused by one or more gaps between modules of an LDA x-ray detector, in accordance with one or more techniques of this disclosure.

FIG. 9A is an example computed tomography image 300 based on radiographs that are not corrected for artifacts caused by one or more gaps between modules of LDA x-ray detector 14. In other words, FIG. 9A is a CT reconstruction slice produced from images that have not been gap corrected. FIG. 9B is an example computed tomography image 302 based on radiographs that are corrected for artifacts caused by one or more gaps between modules of LDA x-ray detector 14, in accordance with one or more techniques of this disclosure. In other words, FIG. 9B is a CT reconstruction slice produced from images that have been gap corrected. As is apparent from FIG. 9A and FIG. 9B, the structure shown in FIG. 9A and FIG. 9B is sharper in FIG. 9B than FIG. 9A.

Figure 10A:
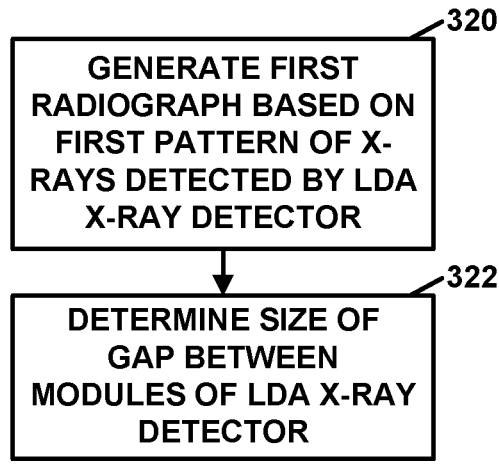
FIG. 10A is a flowchart illustrating an example operation of an x-ray imaging system, in accordance with one or more techniques of this disclosure.

FIG. 10A is a flowchart illustrating an example operation of x-ray imaging system 10, in accordance with one or more techniques of this disclosure. The operation of FIG. 10A and the operation of other flowcharts of this disclosure are merely examples. Other example operations may include more, fewer, or different actions. Furthermore, operations may be performed in different orders or in parallel. Although FIG. 10A and the other flowcharts of this disclosure of described using reference numbers from other figures of this disclosure, the example operations described in the flowcharts are not limited to the examples shown in the other figures. Furthermore, although the example operations of the flowcharts are described with reference to x-rays, the example operations of the flowcharts may be applicable to other types of radiation. Hence, the discussion below of x-ray imaging system 10 may be applicable to other types of imaging systems.

In the example of FIG. 10A, x-ray imaging system 10 generates a first radiograph based on a first pattern of radiation detected by LDA x-ray detector 14 positioned to detect a radiation beam emitted by an x-ray generator 12. LDA x-ray detector 14 comprises a plurality of modules. Each respective module of the plurality of modules comprises a respective plurality of photodiodes corresponding to pixels. Furthermore, x-ray imaging system 10 determines, based on the first radiograph, a size of a gap between two of the modules of LDA x-ray detector 14 (322).

In some examples consistent with the operation of FIG. 10A, x-ray imaging system 10 or another device may move, relative to x-ray generator 12 and LDA x-ray detector 14, at a consistent speed, a target object along a path in a plane parallel to an orientation of LDA x-ray detector 14. As the target object moves along the path, the target object moves through the radiation beam. The first radiograph comprises a line that corresponds to the target object as the target moves along the path. X-ray imaging system 10 may determine a position of the gap based on a position of a discontinuity in a slope of the line. Furthermore, x-ray imaging system 10 may determine the size of the gap based on a size of the discontinuity in the slope of the line. X-ray imaging system 10 may modify, based on the position of the gap and the size of the gap, the second radiograph to compensate for the gap.

In other examples consistent with the operation of FIG. 10A, the first radiograph includes an image of an object having an axis parallel to an orientation of LDA x-ray detector 14. X-ray imaging system 10 may determine, based on a known length of the object in the axis and based on an apparent length of the object in the axis as shown in the first radiograph, the size of the gap. For instance, x-ray imaging system 10 may determine a difference between the known length of the object in the axis and the apparent length of the object. X-ray imaging system 10 may determine that the size of the gap is equal to the difference divided by a known number of gaps between the modules of LDA x-ray detector 14.

Figure 10B:
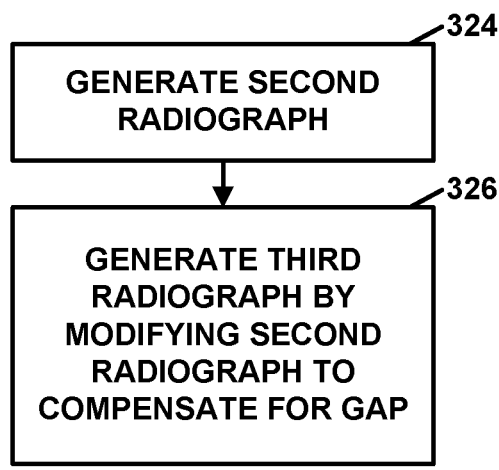
FIG. 10B is a flowchart illustrating an example operation of the x-ray imaging system, in accordance with one or more techniques of this disclosure.

FIG. 10B is a flowchart illustrating an example operation of x-ray imaging system 10, in accordance with one or more techniques of this disclosure. X-ray imaging system 10 may perform the operation of FIG. 10B after determining the size of the gap (e.g., using the operation of FIG. 10A). In the example of FIG. 10B, x-ray imaging system 10 generates a second radiograph based on a second pattern of radiation detected by LDA x-ray detector 14 (324). Furthermore, x-ray imaging system 10 generates a third radiograph (i.e., a modified version of the second radiograph) by modifying, based on the size of the gap, the second radiograph to compensate for the gap (326). In some examples, x-ray imaging system 10 may perform the example operation of FIG. 12 for each pixel to generate the third radiograph. X-ray imaging system 10 may perform the operation of FIG. 10B multiple times without needing to perform the operation of FIG. 10A each time.

Figure 11A:
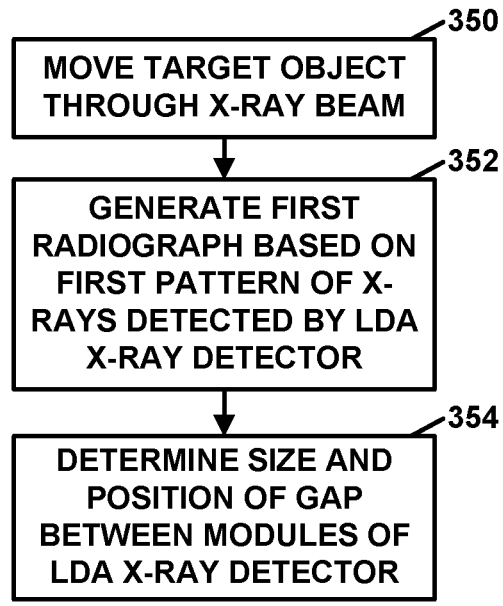
FIG. 11A is a flowchart illustrating another example operation of the x-ray imaging system, in accordance with one or more techniques of this disclosure.

FIG. 11A is a flowchart illustrating an example operation of x-ray imaging system 10, in accordance with one or more techniques of this disclosure. The example operation of FIG. 11A is a more detailed implementation of the example operation of FIG. 10A. In the example of FIG. 11A, x-ray imaging system 10 moves a target object relative to x-ray generator 12 and LDA x-ray detector 14 through an x-ray beam emitted by x-ray generator 12 (350). Note that not all implementations of the example operation of FIG. 10A involve the movement of the target object relative to x-ray generator 12 and LDA x-ray detector 14. In the example, of FIG. 11A, the target object may move along a path at a consistent speed in a first dimension. In some examples, the target object does not move in a second dimension or a third dimension. In the example of FIG. 11A, the first, second, and third dimensions are mutually orthogonal, the first dimension is parallel to an orientation of LDA x-ray detector 14 positioned to detect the x-ray beam, and the third dimension is parallel to an axis between x-ray generator 12 and LDA x-ray detector 14.

Furthermore, in the example of FIG. 11A, image processing system 30 of x-ray imaging system 10 generates, based on a first pattern of x-rays detected by LDA x-ray detector 14, a first radiograph comprising a line corresponding to the target object as the target object moves along the path (352). Image processing system 30 determines, based on a size and a position of a discontinuity in a slope of the line, a size and a position of a gap between two of the modules of LDA x-ray detector 14 (354). For instance, as part of determining the position of the gap, image processing system 30 may determine that the gap exists at a location corresponding to the discontinuity in the slope of the line. In one example, as part of determining the size of the gap, image processing system 30 may determine the size of the gap based on a distance between a first segment endpoint and a second segment endpoint. In this example, the first segment endpoint is an endpoint of a first segment of the line, the second segment endpoint is an endpoint of a second segment of the line, and the first and second endpoints are adjacent to the discontinuity in the slope of the line.

Figure 11B:
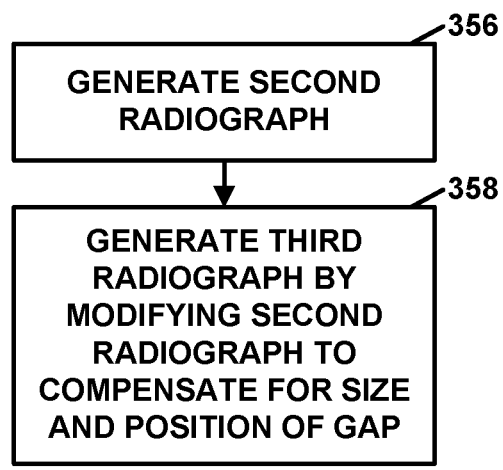
FIG. 11B is a flowchart illustrating another example operation of the x-ray imaging system, in accordance with one or more techniques of this disclosure.

FIG. 11B is a flowchart illustrating an example operation of x-ray imaging system 10, in accordance with one or more techniques of this disclosure. FIG. 11B may be performed after the operation of FIG. 11A is performed. After determining the size and position of a gap (e.g., by performing the operation of FIG. 11A), x-ray imaging system 10 generates, based on a second pattern of x-rays detected by LDA x-ray detector 14, a second radiograph (356). Image processing system 30 of x-ray imaging system 10 may then generate a third radiograph by modifying, based on the size and position of the gap, the second radiograph to compensate for the gap (358). X-ray imaging system 10 may perform the operation of FIG. 11B multiple times without needing to perform the operation of FIG. 11A each time.

Figure 12:
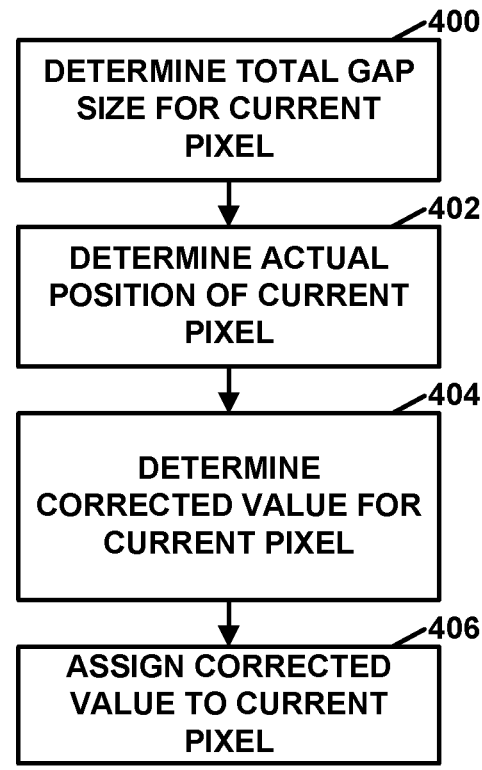
FIG. 12 is a flowchart illustrating an example operation of the x-ray imaging system to modify pixels to compensate for gaps between modules of an LDA x-ray detector, in accordance with one or more techniques of this disclosure.

FIG. 12 is a flowchart illustrating an example operation of x-ray imaging system 10 to modify pixels to compensate for gaps between modules of LDA x-ray detector 14, in accordance with one or more techniques of this disclosure. The operation of FIG. 12 is merely one example. Other example operations to compensate for gaps between modules of LDA x-ray detector 14 may include more, fewer, or different actions. For instance, the example operation of FIG. 12 is explained as being performed by image processing system 30 of x-ray imaging system 10. However, in other examples, one or more other components of x-ray imaging system 10 may perform the operation of FIG. 12.

Image processing system 30 of x-ray imaging system 10 may perform the operation of FIG. 12 for each pixel of a radiograph. In the example of FIG. 12, image processing system 30 determines a total gap size for a current pixel (400). The total gap size for the current pixel is a total size of gaps (if any) prior, in a current row of pixels, to the current pixel. In other words, the total gap size for the current pixel may be a sum of gap sizes for any gaps occurring prior to the current pixel in a row of pixels that includes the current pixel. For example, image processing system 30 may determine that the total gap size for the current pixel is 1.5 pixel sizes.

Furthermore, image processing system 30 may determine, based on the total gap size for the current pixel and the position within the radiograph of the current pixel, an actual position of the current pixel (402). In some examples, the actual position of the current pixel is equal to the position of the current pixel plus the total gap size for the current pixel. Additionally, image processing system 30 may determine a corrected value for the current pixel based on a value of at least one previous pixel, if any, a value of the current pixel, and the actual position of the current pixel (404). For instance, image processing system 30 may estimate (e.g., interpolate), based on the value of the previous picture and the actual location of the current pixel, a value of a pixel occurring adjacent to the previous pixel. In this instance, it is assumed for purposes of interpolation that the current pixel is at the actual position of the current pixel. In some examples, the previous pixel may occur immediately prior to the current pixel in a scanning order used for generating the modified radiograph. For example, the position of the previous pixel may be 10, the position of the current pixel is 11, and the gap size is equal to 1 pixel. In this example, the actual position of the current pixel is 12. Hence, if the value of the previous pixel is 0 and the value of the current pixel is 1, the interpolated value is equal to 0.5. X-ray imaging system 10 may then assign the corrected value for the current pixel to the current pixel (406).

Figure 13:
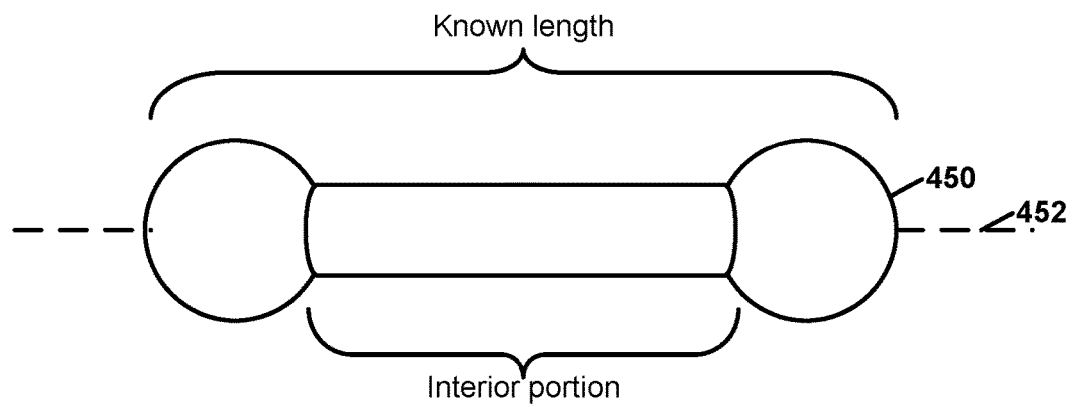
FIG. 13 is a conceptual diagram of an object of known length usable for estimating sizes of gaps between modules of an LDA x-ray detector, in accordance with one or more techniques of this disclosure.

FIG. 13 is a conceptual diagram of an object 450 of known length usable for estimating sizes of gaps between modules of LDA x-ray detector 14, in accordance with one or more techniques of this disclosure. In the example of FIG. 13, object 450 is a dumbbell shaped object. An interior portion of object 450 is cylindrical. However, in other examples, an object used for similar purposes can have other shapes.

A user may mount, or otherwise position, object 450 on stage 26 such that an axis (e.g., long axis 452) of object 450 is aligned with the orientation of LDA x-ray detector 14. LDA x-ray detector 14 may then detect a pattern of x-rays generated by x-ray generator 12. Image processing system 30 may generate a radiograph based on the pattern of x-rays. Image processing system 30 may then compare the length of object 450 as shown in the radiograph with the known length of object 450. The difference between these two lengths is the total size of gaps between modules of LDA x-ray detector 14. In this example, image processing system 30 may have a priori knowledge of the number and positions of gaps. For instance, image processing system 30 may store data indicating that gaps occur intervals of 250 pixels and the sizes of each pixel and gaps between pixels. Furthermore, in this example, image processing system 30 may assume that each of the gaps has the same size. In other words, the assumed size of each of the gaps is equal to the total sizes of the gaps divided by the number of gaps. Image processing system 30 may use this information regarding the positions and sizes of the gaps to modify subsequent radiographs to compensate for the gaps in the manner described elsewhere in this disclosure.

Figure 14A:
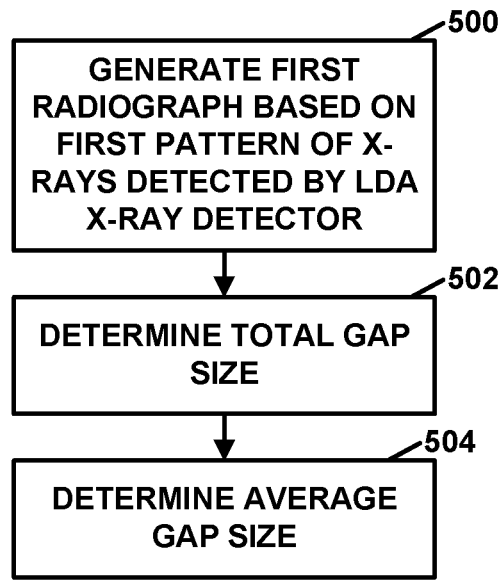
FIG. 14A is a flowchart illustrating another example operation of the x-ray imaging system, in accordance with one or more techniques of this disclosure.

FIG. 14A is a flowchart illustrating an example operation of x-ray imaging system 10, in accordance with one or more techniques of this disclosure. The example operation of FIG. 14A is a more detailed implementation of the example operation of FIG. 10A. In other words, the example operation of FIG. 14A may be an example technique for determining the size of a gap between two of the modules of LDA x-ray detector 14. In the example of FIG. 14A, x-ray imaging system 10 generates a first radiograph based on a first pattern of x-rays detected by LDA x-ray detector 14 (500). The first radiograph includes an image of an object (e.g., object 450) having a known length. A lengthwise axis of the object is aligned with an orientation of LDA x-ray detector 14.

After generating the first radiograph, image processing system 30 of x-ray imaging system 10 determines a total gap size (502). The total gap size may indicate a total size (i.e., width) of gaps between modules of LDA x-ray detector 14. Image processing system 30 may determine the total gap size by comparing the known length of the object and an apparent length of the object in the first radiograph. For example, image processing system 30 may determine the total gap size by subtracting the apparent length from the known length. Next, image processing system 30 may determine an average gap size (504). Image processing system 30 may determine the average gap size by dividing the total gap size by a known number of gaps between modules of LDA x-ray detector.

Figure 14B:
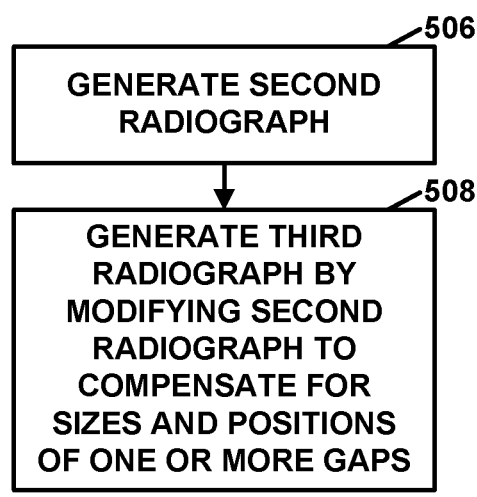
FIG. 14B is a flowchart illustrating another example operation of the x-ray imaging system, in accordance with one or more techniques of this disclosure.

FIG. 14B is a flowchart illustrating another example operation of x-ray imaging system 10, in accordance with one or more techniques of this disclosure. X-ray imaging system 10 may perform the operation of FIG. 14B after determining an average gap size (e.g., using the operation of FIG. 14A). In the example of FIG. 14B, image processing system 30 of x-ray imaging system 10 generates a second radiograph (506). The second radiograph may include an image of a different object. Image processing system 30 may generate a third radiograph (i.e., a modified version of the second radiograph) by modifying the second radiograph to compensate for the sizes and positions of the one or more gaps between modules of LDA x-ray detector 14 (508). X-ray imaging system 10 may perform the operation of FIG. 14B multiple times without needing to perform the operation of FIG. 14A each time.

Figure 15:
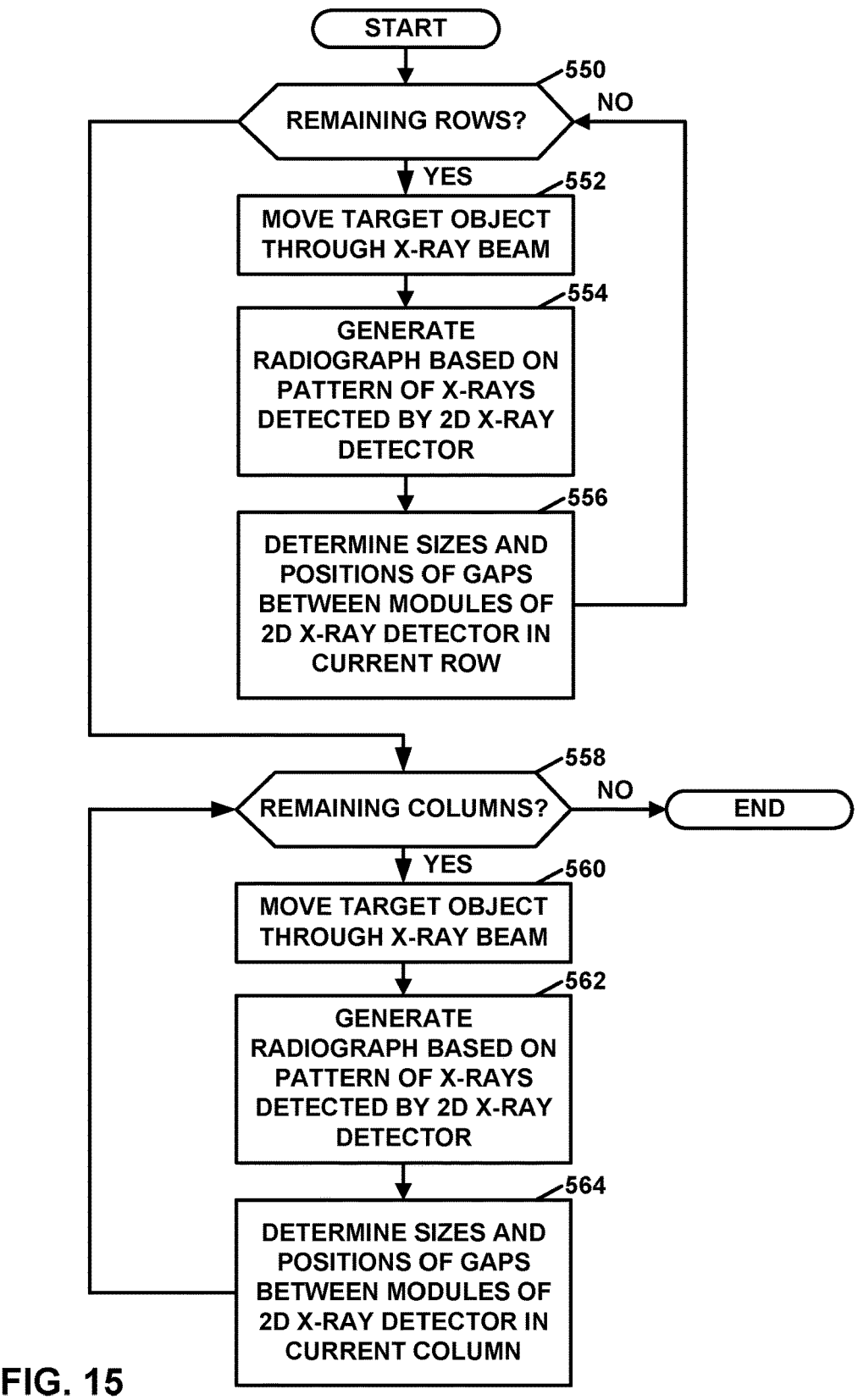
FIG. 15 is a flowchart illustrating an example operation of the x-ray imaging system for calibrating a 2-dimensional x-ray detector, in accordance with one or more techniques of this disclosure.

FIG. 15 is a flowchart illustrating an example operation of x-ray imaging system 10 for calibrating 2D x-ray detector 51, in accordance with one or more techniques of this disclosure. The operation shown in the example of FIG. 15 is similar to that shown in the example of FIG. 11A, except repeated for each row and column of photodiodes of 2D x-ray detector 51.

In the example of FIG. 15, image processing system 30 of x-ray imaging system 10 determines whether there are any remaining rows of photodiodes of 2D x-ray detector 51 to process (550). In response to determining there is a remaining row of photodiodes to process ("YES" branch of 550), x-ray imaging system 10 may move a target object relative to x-ray generator 12 and 2D x-ray detector 51 through an x-ray beam emitted by x-ray generator 12 (552). The target object may move along a path at a consistent speed in a first dimension (e.g., a horizontal dimension). In some examples, the target object does not move in a second dimension or a third dimension. In the example of FIG. 15, the first, second, and third dimensions are mutually orthogonal, the first dimension is parallel to a plane of 2D x-ray detector 51, and the third dimension is parallel to an axis between x-ray generator 12 and 2D x-ray detector 51.

Furthermore, in the example of FIG. 15, image processing system 30 of x-ray imaging system 10 generates, based on a pattern of x-rays detected by 2D x-ray detector 51, a radiograph comprising a line corresponding to the target object as the target object moves along the path (554). Image processing system 30 determines, based on sizes and positions of discontinuities in a slope of the line, sizes and positions of gaps between modules of 2D x-ray detector 14 at the location of the current row (556). For instance, as part of determining the position of the gap, image processing system 30 may determine that the gap exists at a location corresponding to the discontinuity in the slope of the line.

Image processing system 30 may then determine whether there are any remaining unprocessed rows of 2D x-ray detector 51 (550). If so, actions 552-556 may be repeated. In this way, actions 552-556 may be repeated for each row of photodiodes of 2D x-ray detector 51. On the other hand, in response to determining there are no remaining rows ("NO" branch of 550), image processing system 30 determines whether there are any remaining columns of photodiodes of 2D x-ray detector 51 to process (558). In response to determining there is a remaining column of photodiodes to process ("YES" branch of 558), x-ray imaging system 10 may move a target object relative to x-ray generator 12 and 2D x-ray detector 51 through an x-ray beam emitted by x-ray generator 12 (560). The target object may move along a path at a consistent speed in the second dimension (e.g., a vertical dimension). In some examples, the target object does not move in the first dimension or the third dimension.

Furthermore, in the example of FIG. 15, image processing system 30 generates, based on a pattern of x-rays detected by 2D x-ray detector 51, a radiograph comprising a line corresponding to the target object as the target object moves along the path (562). Image processing system 30 determines, based on sizes and positions of discontinuities in a slope of the line, sizes and positions of gaps between modules of 2D x-ray detector 51 at the location of the current column (564). For instance, as part of determining the position of the gap, image processing system 30 may determine that the gap exists at a location corresponding to the discontinuity in the slope of the line. Image processing system 30 may then determine whether there are any remaining unprocessed columns of 2D x-ray detector 51 (558). If so, actions 560-564 may be repeated. In this way, actions 560-564 may be repeated for each column of photodiodes of 2D x-ray detector 51.

After performing the operation of FIG. 15, x-ray imaging system 10 may generate additional radiographs without repeating the operation of FIG. 15. Image processing system 30 may use the information generated by the operation of FIG. 15 regarding positions and sizes of gaps for each row and column to modify the additional radiographs to compensates for the gaps between the modules of 2D x-ray detector 51. For instance, image processing system 30 may perform the example operation of FIG. 16 to compensate for the gaps between the modules of 2D x-ray detector 51 in the additional radiographs.

In this way, x-ray imaging system 10 may generate a first radiograph based on a first pattern of radiation detected by an x-ray detector, such as a LDA x-ray detector 14 or 2D x-ray detector 51, positioned to detect a radiation beam emitted by x-ray generator 12. In either case, the x-ray detector comprises a plurality of modules. Each respective module of the plurality of modules comprises a respective plurality of photodiodes corresponding to pixels. Furthermore, x-ray imaging system 10 may determine, based on the first radiograph, a size of a gap between two of the modules of the x-ray detector. After determining the size of the gap, x-ray imaging system 10 may generate a second radiograph based on a second pattern of radiation detected by the radiation detector. X-ray imaging system 10 may generate a third radiograph by modifying, based on the size of the gap, the second radiograph to compensate for the gap.

In some examples, x-ray imaging system 10 does not move the target object relative to x-ray generator 12 and 2D x-ray detector 51 for each row and column of photodiodes of 2D x-ray detector 51. Rather, in such examples, image processing system 30 may only move the target object relative to x-ray generator 12 and 2D x-ray detector 51 once in the first dimension and once in the second dimension. In such examples, a target object used for the rows may be sized to block or attenuate x-rays for the entire height of 2D x-ray detector 51 and a target object used for the columns may be sized to block or attenuate x-rays for the entire width of 2D x-ray detector 51. Furthermore, in this example, for each respective row of photodiodes of 2D x-ray detector 51, image processing system 30 may generate a respective radiograph based only on the signals from photodiodes of the respective row of photodiodes such that each row of pixels of the respective radiograph corresponds to a different time instance. Likewise, in this example for each respective column of photodiodes of 2D x-ray detector 51, image processing system 30 may generate a respective radiograph based only on the signals from photodiodes of the respective column of photodiodes such that each column of pixels of the respective radiograph corresponds to a different time instance.

Figure 16:
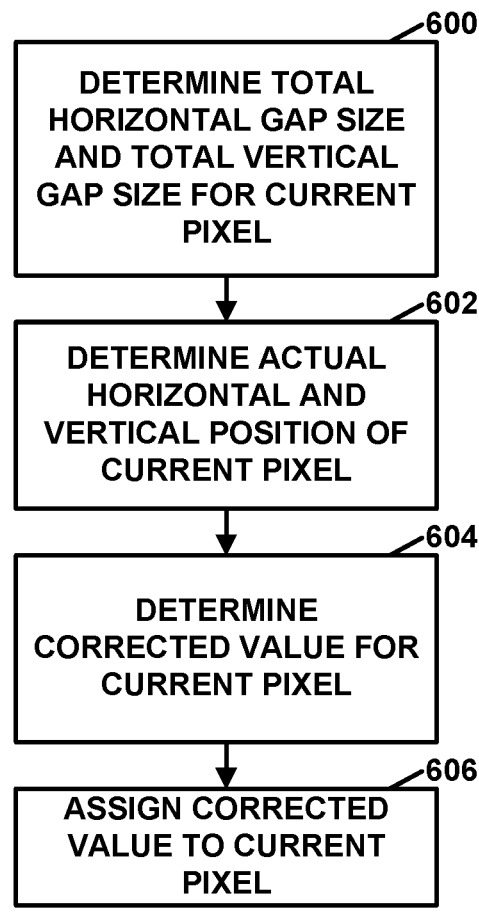
FIG. 16 is a flowchart illustrating an example operation of the x-ray imaging system for compensating for gaps between modules of the 2-dimensional x-ray detector, in accordance with one or more techniques of this disclosure.

FIG. 16 is a flowchart illustrating an example operation of x-ray imaging system 10 for compensating for gaps between modules of 2-dimensional x-ray detector 51, in accordance with one or more techniques of this disclosure. Image processing system 30 of x-ray imaging system 10 may perform the operation of FIG. 16 for each pixel of a radiograph. In the example of FIG. 16, image processing system 30 determines a total horizontal gap size for a current pixel and a total vertical gap size for the current pixel (600). The total horizontal gap size for the current pixel is a total size of gaps (if any) prior, in a current row of pixels, to the current pixel. In other words, the total horizontal gap size for the current pixel may be a sum of gap sizes for any gaps occurring prior to the current pixel in a row of pixels that includes the current pixel. The total vertical gap size for the current pixel is a total size of gaps (if any) prior, in a current column of pixels, to the current pixel. In other words, the total vertical gap size for the current pixel may be a sum of gap sizes for any gaps occurring prior to the current pixel in a column of pixels that includes the current pixel.

Furthermore, image processing system 30 may determine, based on the total horizontal gap size and the total vertical gap size for the current pixel and the position within the radiograph of the current pixel, an actual horizontal position and actual vertical position of the current pixel (602). In some examples, the actual horizontal position of the current pixel is equal to the horizontal position of the current pixel plus the total horizontal gap size for the current pixel. The actual vertical position of the current pixel is equal to the vertical position of the current pixel plus the total vertical gap size for the current pixel.

Additionally, image processing system 30 may determine a corrected value for the current pixel based on a value of at least one previous horizontal pixel, if any, a previous vertical pixel, if any, a value of the current pixel, and the actual position of the current pixel (604). For instance, image processing system 30 may estimate (e.g., interpolate) a value of a pixel occurring adjacent to the previous horizontal and vertical pixels, where it is assumed that the current pixel is at the actual position of the current pixel. X-ray imaging system 10 may then assign the corrected value for the current pixel to the current pixel (606).

Although the techniques of this disclosure have been described with reference to x-rays, the techniques of this disclosure may also be applicable to other wavelengths, such as visible light, microwaves, ultraviolet radiation, infrared radiation, and so on.

The techniques of this disclosure may be implemented in a wide variety of devices or apparatuses. Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

In one or more examples, particular functions described may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transitory, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. In addition, in some aspects, the functionality described herein may be provided within dedicated hardware and/or software modules. Also, particular portions of the techniques may be implemented in one or more circuits or logic elements.

Various examples have been described. These and other examples are within the scope of the following claims.

What is claimed is:

1. A method for generating radiographs, the method comprising:
   generating, by an imaging system, a first radiograph based on a first pattern of radiation detected by a Linear Diode Array (LDA) radiation detector positioned to detect a radiation beam emitted by a radiation generator, wherein:
      the LDA radiation detector comprises a plurality of modules, and
      each respective module of the plurality of modules comprises a respective plurality of photodiodes corresponding to pixels;
   determining, by the imaging system, based on the first radiograph, a size of a gap between two of the modules of the LDA radiation detector; and
   after determining the size of the gap:
      generating, by the imaging system, a second radiograph based on a second pattern of radiation detected by the LDA radiation detector; and
      generating, by the imaging system, a third radiograph by modifying, based on the size of the gap, the second radiograph to compensate for the gap.

2. The method of claim 1, further comprising:
   moving, by the imaging system, relative to the radiation generator and the LDA radiation detector, at a consistent speed, a target object along a path in a plane parallel to an orientation of the LDA radiation detector, wherein, as the target object moves along the path, the target object moves through the radiation beam, and wherein the first radiograph comprises a line that corresponds to the target object as the target moves along the path; and
   determining, by the imaging system, a position of the gap based on a position of a discontinuity in a slope of the line,
   wherein determining the size of the gap comprises determining, by the imaging system, the size of the gap based on a size of the discontinuity in the slope of the line, and
   wherein generating the third radiograph comprises modifying, based on the position of the gap and the size of the gap, the second radiograph to compensate for the gap.

3. The method of claim 2, wherein generating the third radiograph comprises:
   determining, by the imaging system, a total gap size for a current pixel of the second radiograph, the total gap size for the current pixel being a sum of gap sizes for any gaps occurring prior to the current pixel in a row of pixels that includes the current pixel;
   determining, by the imaging system, based on the total gap size for the current pixel and a position within the second radiograph of the current pixel, an actual position of the current pixel;
   determining, by the imaging system, a corrected value for the current pixel based on a value of a previous pixel, if any, a value of the current pixel, and the actual position of the current pixel; and
   assigning, by the imaging system, the corrected value for the current pixel to the current pixel.

4. The method of claim 3, wherein the previous pixel occurs immediately prior to the current pixel in a scanning order used for generating the third radiograph.

5. The method of claim 3, the determination of the corrected value assumes the current pixel is at the actual position of the current pixel.

6. The method of claim 3, wherein the actual position for the current pixel is equal to the position of the current pixel plus the total gap size for the current pixel.

7. The method of claim 2, wherein:
   determining the position of the gap comprises:
      determining, by the imaging system, that the gap exists at a location corresponding to the discontinuity in the slope of the line; and
   determining the size of the gap comprises:
      determining, by the imaging system, the size of the gap based on a distance between a first segment endpoint and a second segment endpoint, the first segment endpoint being an endpoint of a first segment of the line, the second segment endpoint being an endpoint of a second segment of the line, the first and second endpoints being adjacent to the discontinuity.

8. The method of claim 2, wherein:
   the radiation generator and the LDA radiation detector are mounted to one or more frames; and
   moving the target object comprises:
      moving, by the imaging system, the target object relative to the one or more frames without moving the radiation generator and the LDA radiation detector relative to the one or more frames.

9. The method of claim 2, wherein:
   the radiation generator and the LDA radiation detector are mounted to one or more frames; and
   moving the target object comprises:
      moving, by the imaging system, both the radiation generator and the LDA radiation detector relative to the one or more frames without moving the target object relative to the one or more frames.

10. The method of claim 2, wherein the plane is orthogonal to an axis between the radiation generator and the LDA radiation detector.

11. The method of claim 1, wherein:
   the first radiograph includes an image of an object having an axis parallel to an orientation of the LDA radiation detector, and
   determining the size of the gap comprises:
      determining, by the imaging system, based on a known length of the object in the axis and based on an apparent length of the object in the axis as shown in the first radiograph, the size of the gap.

12. The method of claim 11, wherein determining the size of the gap comprises:
   determining, by the imaging system, a difference between the known length of the object in the axis and the apparent length of the object; and determining, by the imaging system, that the size of the gap is equal to the difference divided by a known number of gaps between the modules of the LDA radiation detector.

13. An imaging system comprising:
a radiation generator;
a Linear Diode Array (LDA) radiation detector positioned to detect a radiation beam emitted by the radiation generator, the LDA radiation detector comprising a plurality of modules, wherein each of the modules comprises a respective plurality of photodiodes corresponding to pixels; and
one or more processors operatively coupled to the LDA radiation detector, the one or more processors configured to:
generate a first radiograph based on a first pattern of radiation detected by the LDA radiation detector;
determine, based on the first radiograph, a size of a gap between two of the modules of the LDA radiation detector; and
after determining the size of the gap:
generate a second radiograph based on a second pattern of radiation detected by the LDA radiation detector; and
generate a third radiograph by modifying, based on the size of the gap, the second radiograph to compensate for the gap.

14. The imaging system of claim 13, further comprising:
one or more manipulator mechanisms; and
wherein the one or more processors are configured:
activate the one or more manipulator mechanisms to move, relative to the radiation generator and the LDA radiation detector, a target object along a path in a plane parallel to an orientation of the LDA radiation detector, wherein:
the target object moves through the radiation beam as the target object moves along the path, and
the first radiograph comprises a line corresponding to the target object as the target object moves along the path;
determine a position of the gap based on a position of a discontinuity in a slope of the line,
wherein as part of determining the size of the gap, the one or more processors determine the size of the gap based on a size of the discontinuity in the slope of the line, and
wherein as part of generating the third radiograph, the one or more processors modify, based on the position of the gap and the size of the gap, the second radiograph to compensate for the gap.

15. The imaging system of claim 14, wherein to generate the third radiograph, the one or more processors:
determine a total gap size for a current pixel of the second radiograph, the total gap size for the current pixel being a sum of gap sizes for any gaps occurring prior to the current pixel in a row of pixels that includes the current pixel;
determine, based on the total gap size for the current pixel and a position within the second radiograph of the current pixel, an actual position of the current pixel;
determine a corrected value for the current pixel based on a value of a previous pixel, if any, a value of the current pixel, and the actual position of the current pixel; and
assign the corrected value for the current pixel to the current pixel.

16. The imaging system of claim 14, wherein the previous pixel occurs immediately prior to the current pixel in a scanning order used for generating the third radiograph.

17. The imaging system of claim 14, wherein the actual position of the current pixel is equal to the position of the current pixel plus the total gap size for the current pixel.

18. The imaging system of claim 14, wherein to determine the size and position of the gap, the one or more processors:
determine that the gap exists at a location corresponding to the discontinuity in the slope of the line; and
determine the size of the gap based on a distance between a first segment endpoint and a second segment endpoint, the first segment endpoint being an endpoint of a first segment of the line, the second segment endpoint being an endpoint of a second segment of the line, the first and second endpoints being adjacent to the discontinuity.

19. The imaging system of claim 14, further comprising one or more frames to which the radiation generator and the LDA radiation detector are mounted, wherein the one or more processors are configured to activate the one or more manipulator mechanisms to move the target object relative to the one or more frames without moving the radiation generator and the LDA radiation detector relative to the one or more frames.

20. The imaging system of claim 14, further comprising one or more frames to which the radiation generator and the LDA radiation detector are mounted, wherein the one or more processors are configured to activate the one or more manipulator mechanisms to move both the radiation generator and the LDA radiation detector relative to the one or more frames without moving the target object relative to the one or more frames.

21. The imaging system of claim 14, wherein the plane is orthogonal to an axis between the radiation generator and the LDA radiation detector.

22. The imaging system of claim 13, wherein:
the first radiograph includes an image of an object having an axis parallel to an orientation of the LDA radiation detector, and
as part of determining the size of the gap, the one or more processors determine, based on a known length of the object in the axis and based on an apparent length of the object in the axis as shown in the first radiograph, the size of the gap.

23. The imaging system of claim 22, wherein as part of determining the size of the gap, the one or more processors:
determine a difference between the known length of the object in the axis and the apparent length of the object; and
determine that the size of the gap is equal to the difference divided by a known number of gaps between the modules of the LDA radiation detector.

24. A non-transitory computer-readable data storage medium having instructions stored thereon that, when executed, cause an imaging system to:
generate a first radiograph based on a first pattern of radiation detected by a Linear Diode Array (LDA) radiation detector positioned to detect a radiation beam emitted by a radiation generator, wherein:
the LDA radiation detector comprises a plurality of modules, and
each respective module of the plurality of modules comprises a respective plurality of photodiodes corresponding to pixels;

determine, based on the first radiograph, a size of a gap between two of the modules of the LDA radiation detector; and after determining the size of the gap:
generate, based on a second pattern of radiation detected by the LDA radiation detector, a second radiograph; and
generate a third radiograph by modifying, based on the size of the gap, the second radiograph to compensate for the gap.

25. A method for generating radiographs, the method comprising:
generating, by an imaging system, a first radiograph based on a first pattern of radiation detected by a 2-dimensional radiation detector positioned to detect a radiation beam emitted by a radiation generator, wherein:
the 2-dimensional radiation detector comprises a plurality of modules, and
each respective module of the plurality of modules comprises a respective plurality of photodiodes corresponding to pixels;
determining, by the imaging system, based on the first radiograph, a size of a gap between two of the modules of the 2-dimensional radiation detector; and
after determining the size of the gap:
generating, by the imaging system, a second radiograph based on a second pattern of radiation detected by the 2-dimensional radiation detector; and
generating, by the imaging system, a third radiograph by modifying, based on the size of the gap, the second radiograph to compensate for the gap.

26. An imaging system comprising:
a radiation generator;
a 2-dimensional radiation detector positioned to detect a radiation beam emitted by the radiation generator, the 2-dimensional radiation detector comprising a plurality of modules, wherein each of the modules comprises a respective plurality of photodiodes corresponding to pixels; and
one or more processors operatively coupled to the 2-dimensional radiation detector, the one or more processors configured to:
generate a first radiograph based on a first pattern of radiation detected by the 2-dimensional radiation detector;
determine, based on the first radiograph, a size of a gap between two of the modules of the 2-dimensional radiation detector; and
after determining the size of the gap:
generate a second radiograph based on a second pattern of radiation detected by the 2-dimensional radiation detector; and
generate a third radiograph by modifying, based on the size of the gap, the second radiograph to compensate for the gap.

27. A non-transitory computer-readable data storage medium having instructions stored thereon that, when executed, cause an imaging system to:
generate a first radiograph based on a first pattern of radiation detected by a 2-dimensional radiation detector positioned to detect a radiation beam emitted by a radiation generator, wherein:
the 2-dimensional radiation detector comprises a plurality of modules, and
each respective module of the plurality of modules comprises a respective plurality of photodiodes corresponding to pixels;
determine, based on the first radiograph, a size of a gap between two of the modules of the 2-dimensional radiation detector; and
after determining the size of the gap:
generate, based on a second pattern of radiation detected by the 2-dimensional radiation detector, a second radiograph; and
generate a third radiograph by modifying, based on the size of the gap, the second radiograph to compensate for the gap.

* * * * *